(12) United States Patent
Chu et al.

(10) Patent No.: US 8,231,013 B2
(45) Date of Patent: Jul. 31, 2012

(54) ARTICLES COMPRISING A FIBROUS SUPPORT

(75) Inventors: Benjamin Chu, Setauket, NY (US);
Benjamin Hsiao, Setauket, NY (US);
Kyunghwan Yoon, East Setauket, NY (US)

(73) Assignee: The Research Foundation of State University of New York, Albany, NY (US)

( * ) Notice: Subject to any disclaimer, the term of this patent is extended or adjusted under 35 U.S.C. 154(b) by 408 days.

(21) Appl. No.: 11/951,248

(22) Filed: Dec. 5, 2007

(65) Prior Publication Data
US 2008/0149561 A1    Jun. 26, 2008

Related U.S. Application Data

(60) Provisional application No. 60/873,086, filed on Dec. 6, 2006, provisional application No. 60/872,891, filed on Dec. 5, 2006.

(51) Int. Cl.
*B01D 24/00* (2006.01)
*B01D 39/00* (2006.01)
*B01D 39/14* (2006.01)
*B01D 63/00* (2006.01)
*B01D 71/00* (2006.01)
*B01D 71/04* (2006.01)
*B01D 71/06* (2006.01)

(52) U.S. Cl. ........... 210/500.1; 210/500.21; 210/500.26; 210/500.27; 210/500.38; 210/501; 210/502.1; 210/503; 210/504; 210/505; 210/508

(58) Field of Classification Search .................. None
See application file for complete search history.

(56) References Cited

U.S. PATENT DOCUMENTS

| 5,049,167 | A | | 9/1991 | Castro et al. |
| 6,162,358 | A | * | 12/2000 | Li et al. ............. 210/500.38 |
| 6,536,605 | B2 | * | 3/2003 | Rice et al. .................... 210/490 |
| 7,090,712 | B2 | * | 8/2006 | Gillingham et al. .......... 55/486 |
| 7,211,320 | B1 | * | 5/2007 | Cooper et ................ 428/306.6 |
| 7,304,125 | B2 | * | 12/2007 | Ibar ........................ 528/502 R |
| 2002/0014182 | A1 | | 2/2002 | Yadav et al. |
| 2005/0133455 | A1 | * | 6/2005 | Witham et al. ............ 210/721 |

OTHER PUBLICATIONS

Young, "International Search Report," 2 pages, from International Patent Application No. PCT/US07/86549 (mailed Sep. 17, 2008).

* cited by examiner

*Primary Examiner* — Benjamin Kurtz
(74) *Attorney, Agent, or Firm* — Carter, DeLuca, Farrell & Schmidt, LLP

(57) ABSTRACT

Articles comprising a fibrous support of nanofibers and an interfacially polymerized polymer layer disposed on a surface of the fibrous support are useful, e.g., as fluid separation membranes.

31 Claims, 17 Drawing Sheets

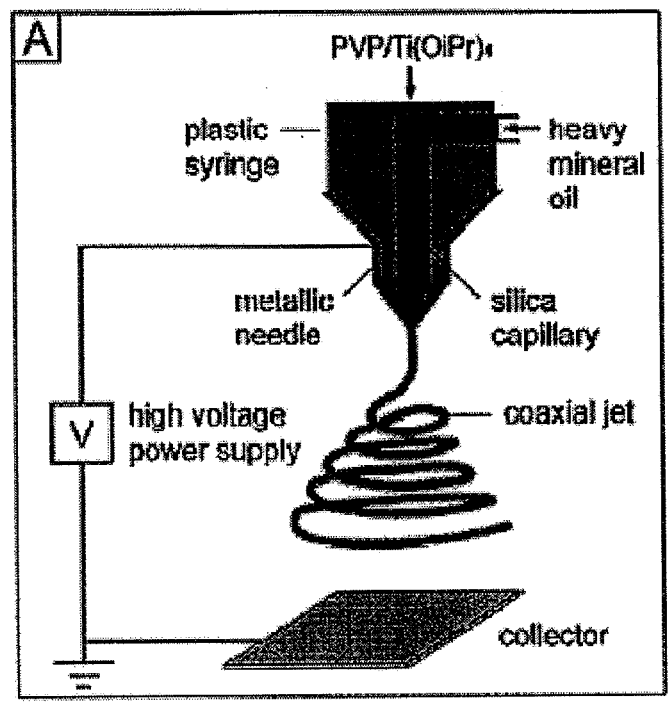
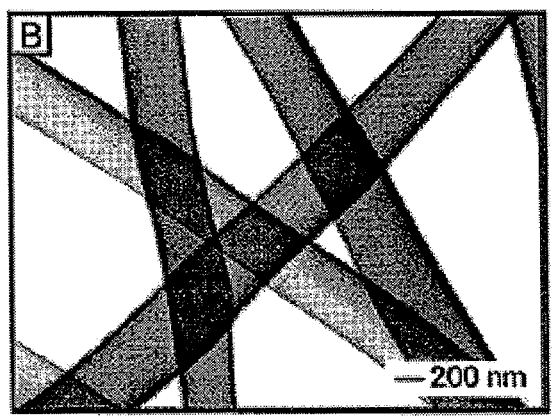
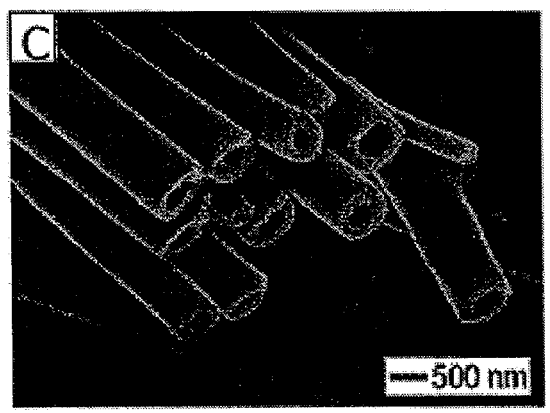
Figure 31A-C

| | Rejection (%) = $(1-C_p/C_F) \times 100$ | | | |
|---|---|---|---|---|
| Molecular Weights (g/mol) | 100k-200k | 64k-76k | 35k-45k | 9k-11k |
| PAN400 (Sepro) | 30.8 ± 4.3 (%) | 9.8 ± 4.9 (%) | 8.0 ± 1.7 (%) | 7.3 ± 1.8 (%) |
| PAN10 (Sepro) | 93 ± 3 (%) | 92 ± 3 (%) | 89 ± 1.3 (%) | 70 ± 5 (%) |
| PVA-PAN e-spun | 96 ± 3 (%) | 95 ± 4 (%) | 94 ± 2 (%) | 82 ± 3 (%) |

CF : Feed concentration, CP : Permeate concentration

TABLE 1

FIGURE 32

ARTICLES COMPRISING A FIBROUS SUPPORT

CROSS-REFERENCE TO RELATED APPLICATIONS

This application claims the benefit of U.S. Provisional Patent Application Nos. 60/873,086 filed Dec. 6, 2006 and 60/872,891 filed Dec. 5, 2006, the entire disclosures of which are herein incorporated by reference in their entirety for all purposes.

GOVERNMENT RIGHTS

This invention was made with Government support under the Office of Naval Research, grant number N000140310932. The Government has certain rights in the invention.

FIELD OF THE INVENTION

The present invention relates to articles comprising a fibrous support comprising nanofibers and an interfacially polymerized polymer layer disposed on the surface of the fibrous support. Articles of the present invention are useful as fluid separation membranes such as ultrafiltration membranes, nanofiltration membranes, reverse osmosis membranes, and forward osmosis membranes.

BACKGROUND OF THE INVENTION

With the continuous decline of available freshwater supplies, the recycling of municipal, industrial, and commercial wastewaters has gained more and more interest in recent years. Accordingly, various membrane-based liquid filtration/separation technologies such as nanofiltration (NF), ultrafiltration (UF), and reverse osmosis (RO) have become ever more important in water treatment applications, such as oil/water emulsion separation and water desalination. Although the commercially available NF, UF, and RO membranes and membrane systems are effective in removing impurities such as small particles, (bio)macromolecules, oily microemulsions, and salts, these membranes often suffer from low flux due to limited permeability. In addition, as the pores of the membranes become clogged (fouled), the flux rate of the membrane decreases during use, making them less and less effective over time. It is therefore desirable to provide higher flux, low fouling membranes for fluid (e.g., water) treatment applications.

Various types of UF, NF, and RO membranes are known, including flat sheet and hollow fiber membranes prepared by phase-inversion or temperature inversion processes using polymeric solutions cast onto porous substrates, and thin film composite membranes prepared by depositing a thin polymer film onto a porous substrate.

In conventional thin film composite membranes, the selective top layer coating has been made primarily by the interfacial polymerization of poly(amino) and poly(acid chloride) monomers onto a porous substrate (e.g., an ultrafiltration or microporous membrane). After Cadotte's pioneering work (e.g., U.S. Pat. No. 4,039,440, herein incorporated by reference in its entirety for all purposes), there have been numerous attempts to improve the performance of UF, NF and RO membranes by interfacial polymerization.

Almost all commercial reverse osmosis (RO) membranes currently used for desalination are composite membranes made by an interfacial polymerization process. Typically, a microporous membrane (e.g., a polysulfone UF membrane) is first soaked in an amine solution. The aromatic amine-wetted UF membrane support is then contacted with one or more crosslinking agents dissolved in an immiscible organic solvent(s) (e.g., trimesoyl chloride in hexane). At the interface of the two immiscible liquids, a dense, crosslinked, and charged polymeric network is formed. Such interfacially polymerized top coating layers typically have a thickness of ~0.002 to ~0.3 µm. Current commercial RO membranes have the sodium chloride rejection rate of 99+% and a water flux greater than 35 L/m$^2$ h at a feed pressure of 800 psi.

The majority of commercially available nanofiltration (NF) membranes are also prepared by interfacial polymerization, e.g., comprising a piperazineamide on a microporous substrate. For example, Cadotte et al. (U.S. Pat. No. 4,259,183, herein incorporated by reference in its entirety for all purposes) has successfully demonstrated the fabrication of NF membranes by the interfacial polymerization of piperazine using trimesoyl chloride. These composite nanofiltration membranes exhibited very high $MgSO_4$ rejection rate (99%) but low NaCl retention rate (<60%). Multi-component (piperazine and polyvinyl alcohol, JP 61 93,806; herein incorporated by reference in its entirety for all purposes) and multi-layer coating (sulfonated polysulfone and piperazineamide) composite membranes have also been prepared. For typical nanofiltration membranes, the molecular weight cutoff ranges are from 100 to 5000 Dalton, with a high rejection of divalent ions (>99%) and low rejection of monovalent ions (~50% or less).

Composite UF membranes have also been prepared by interfacial polymerization. Wrasidlo et al (U.S. Pat. No. 4,902,424, herein incorporated by reference in its entirety for all purposes) prepared composite UF membranes by the interfacial polymerization of a polyethyleneimine-soaked microporous membrane with isophthaloyl chloride and toluene diisocyanate in hexane. The polymerized top coating layer had a thickness ranging from 0.0012 to 0.15 µm, with molecular weight cutoff values ranging from 500 to 1,000,000 Dalton. Stengaard et al (J. Membr. Sci., 53 (1990) 189-202; herein incorporated by reference in its entirety for all purposes) reported reacting an undisclosed aqueous monomer composition with diisocyanates on polyethersulfone UF membranes (MWCO: 20 k~50 k Dalton). Separation of whey/skimmed milk mixtures were carried out, with a permeate flux ranging from 40~75 L/m$^2$ h at 30~60 psi.

Interfacial polymerization methods are suitable for continuous mass production processes because of the rapid reaction kinetics (e.g. poly(hexamethylene sebacamide of high molecular weight has been made in less than 0.02 sec. *Condensation Polymers: by Interfacial and Solution Methods*, P. W. Morgan, John Wiley & Sons, 1965, and because only few steps are needed to complete the coating process: (i) soaking & squeezing, (ii) applying the crosslinking solutions and (iii) decanting the excess solution and drying. Varieties of reactive monomer selections make it possible to fine-tune the filtration spectrum from reverse osmosis to ultrafiltration range.

However, a major drawback in conventional composite membranes prepared by interfacial polymerization processes is pore blockage in the microporous membrane support when it is soaked in aqueous amine solutions. The blocked pores tend to increase the effective coating thickness of the interfacially polymerized coating layer, and consequently tend to decrease the permeate flux. Also, the chemical nature of polyamide coating (e.g. hydrolyzed acyl halide; carboxylate groups and terminating amine groups), make interfacially polyamide composite membranes more prone to fouling by charged solute species, which also tends to significantly reduce the permeate flux. Typically, before the use of interfacially polymerized polyamide coated membrane in the final step of filtration (NF and RO), the feed solution must be pre-filtered by microfiltration and ultrafiltration in order to keep a stable flux rate without significant fouling.

Nanofibrous supports have been studied for many potential applications, such as biomedical scaffolds and as filters. Because of their small fiber size (diameters of around 100 nm), highly interconnected pore structures, and large void volume ($\geq 60\%$), nanofibrous sheets can be used as microfiltration membranes (e.g., Gopal et al, J. Membr. Sci. 281 (2006) 581-586; herein incorporated by reference in its entirety for all purposes), but lack the selective coating layer required for UF, NF, or RO applications.

Therefore, there is a need for high-flux UF, NF, and RO membranes having a high permeation rate, high rejection ratio, and a reduced fouling rate compared to filtration systems currently available on the market today. The composite nanofibrous articles of the present invention provide significantly improved performance compared to existing filtration systems, and exhibit high flux rates, excellent permeation rejection ratio and reduced fouling.

SUMMARY OF THE INVENTION

In one embodiment, the present invention is directed to an article comprising a fibrous support comprising nanofibers, and an interfacially polymerized polymer layer disposed on a surface of the fibrous support.

In another embodiment, the present invention is directed to an article comprising a fibrous support comprising nanofibers, and an interfacially polymerized polymer layer disposed on the surface of the fibrous support, wherein the fibrous support is in the form of a sheet comprising a top layer and the bottom layer, the top layer is disposed between the interfacially polymerized polymer layer and the bottom layer, and the average diameter of the nanofibers of the top layer is less than the average diameter of the nanofibers of the bottom layer.

In yet another embodiment, the present invention is directed to an article comprising a fibrous support comprising nanofibers, an interfacially polymerized polymer layer disposed on a surface of the fibrous support, wherein the interfacially polymerized polymer layer further comprises a nanoparticulate filler.

In still another embodiment, the present invention is directed to ultrafiltration, nanofiltration, reverse osmosis, or forward osmosis membranes comprising a fibrous support comprising nanofibers, and an interfacially polymerized polymer layer disposed on a surface of the fibrous support.

In still yet another embodiment, the present invention is directed to method comprising:

forming a fibrous support comprising nanofibers;

depositing a first solution comprising at least one first polyfunctional monomer dissolved in a first solvent onto the fibrous support, thereby forming a fibrous support wetted with the first solution;

depositing a second solution comprising at least one second polyfunctional monomer dissolved in a second solvent onto the fibrous support wetted with the first solution,
  wherein the at least one second polyfunctional monomers reacts with the at least one first polyfunctional monomer and the first solvent and second solvent are substantially immiscible in each other;

allowing the first polyfunctional monomer to react with the second polyfunctional monomer, thereby forming an interfacially polymerized polymer layer at the interface between the first solvent and the second solvent;

removing excess first and second polyfunctional monomers; and removing the first and second solvents.

BRIEF DESCRIPTION OF THE DRAWINGS

FIG. 31A shows a diagram of an apparatus for electro-spinning core/shell nanofibers.

FIGS. 31B-C are micrographs of hollow nanofibers.

FIG. 32 includes a table, Table 1, which shows the sieving ability (Molecular Weight Cut-off) comparison of PVA-coated PAN e-spun membrane using dextrans.

Figure 1:
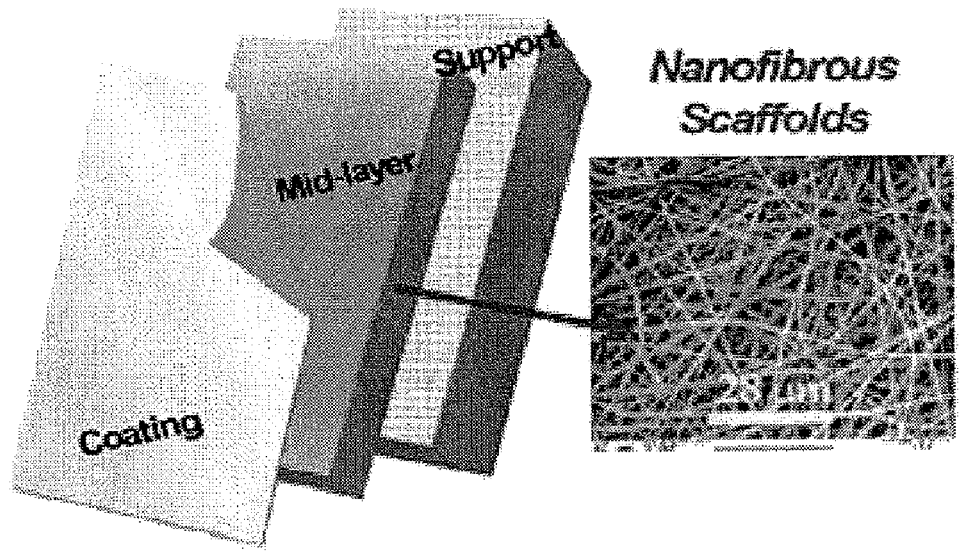
FIG. 1 illustrates a three-tier high flux and low-fouling ultra-filtration membrane of the present invention.

Table 1 shows the sieving ability (Molecular Weight Cut-off) comparison of PVA-coated PAN e-spun membrane using dextrans

DETAILED DESCRIPTION OF THE INVENTION

In one embodiment, the present invention is directed to an article comprising a fibrous support comprising nanofibers, and an interfacially polymerized polymer layer disposed on the surface of the fibrous support, as described herein.

The fibrous support can comprise a symmetric or an asymmetric arrangement of nanofibers. A "symmetric" arrangement of nanofibers means that the average diameter of the nanofibers in any unit volume of the fibrous support is essentially the same.

An "asymmetric" arrangement of nanofibers means that the average diameter of the nanofibers in some portions of the fibrous support differs appreciably from the average diameter of the nanofibers in other portions of the fibrous support. For example, the fibrous support can be in the form of a sheet having at least two layers such that one layer (i.e. the "top layer") is disposed on the top face of the sheet, another layer (i.e., the "bottom layer") is disposed on the bottom face of the sheet, and optionally one or more additional layers (i.e., "middle layers") are disposed between the top and bottom layers of the fibrous support, wherein the nanofibers comprising at least one of the layers has an average fiber diameter which is different from the average fiber diameter of the nanofibers of another layer.

"Asymmetric" fibrous supports also include structures in which the average diameter of the nanofibers increase more or less continuously from one surface of the fibrous support to the opposing surface. For example, fibrous supports of the present invention can be formed by simultaneously forming nanofibers of two or more different average fiber diameters into a non-woven structure. By varying the relative rates at which the different nanofibers are formed, an asymmetric structure can be prepared in which the fiber diameter changes continuously from one surface to the opposing surface. The rate of change of the average fiber diameter through the thickness of the fiber support can be "slow" or relatively abrupt. It will be recognized that the term "layer" refers to a region of the support in which the average fiber diameter is relatively constant, but need not be sharply defined.

In an alternative embodiment, an asymmetric arrangement of nanofibers can be provided by arranging nanofibers of the same average fiber diameter at different packing densities within the fibrous support. For example, the various layers of the fibrous support can be prepared from nanofibers of essentially the same average fiber diameter, except that the percentage of the total volume of each layer occupied by the nanofibers can differ.

The average diameter of the nanofibers of the fibrous support of the present invention ranges from about 2 nm to about 2000 nm, in some embodiments about 10 nm to about 500 nm, and in other embodiments about 20 nm to about 250 nm. The nanofibers are positioned throughout the fibrous support in such a way as to produce a multiplicity of voids. The structure of the fibrous support resembles spinodal decomposition in that it is "bi-continuous" and interconnected. The term "bi-continuous" refers to the interconnection of each phase in a two-phase system, such as one encounters in critical phenomena of a one component (gas-liquid) or two component (binary fluid) system undergoing spinodal decomposition. In the present invention, the nanofibers and the voids each occupy a three dimensional space that is continuous, such that the nanofibers and the voids are continuous.

The nanofibers themselves can be solid, hollow, or have a core-shell structure such that the composition of the outer surface of the nanofiber is different from the composition of the inner portion of the nanofiber.

For example, in one embodiment, one or more of the nanofibers of the fibrous support can be hollow such that the central void in the hollow format occupies about 1% to about 90% of the total volume of the nanofiber.

In an alternative embodiment, one or more of the nanofibers can have a core-shell structure, wherein the volume of the core of the core-shell structure occupies from about 1% to about 90% of the total volume of the nanofiber. The core-shell nanofiber structure can be fabricated as shown in FIG. 31, and contain a heavy mineral oil (FIG. 31A), which can be leached out to produce hollow nanofibers, as shown in FIGS. 31B and 31C. Alternatively the core can comprise a polymer which is different from the polymer comprising the shell of the nanofiber. Core-shell nanofibers comprised of two or more different polymers can be prepared from two different polymer solutions as described herein.

In another alternative embodiment, the same polymer can be used in the core and the shell of a core-shell nanofiber, except that the core or shell layers further comprise additional ingredients. For example, such core-shell nanofibers can be prepared from polymers such as PVP, where the shell layer further comprises amorphorous $TiO_2$. In yet another embodiment, a core-shell nanofiber can have a polymeric shell containing an additive, and an extractable core, which can be extracted to provide a hollow nanofiber with an additive-containing shell layer. For example, such nanofibers can be prepared with a PVP shell further comprising amorphous $TiO_2$ and an oil core. After extraction of the oil core, the resulting hollow nanofibers may be useful for a wide range of applications including but not limited to membrane separation processes, nanofluidics and hydrogen storage. The skilled artisan will appreciate that polymers other than PVP and additives other than amorphous $TiO_2$ could be used depending upon the desired application. Non-limiting examples of such polymers and additives include those disclosed herein. As described herein, the chemical properties of the nanofibers can be modified by appropriate selection of the polymers and additives used, in order to provide the desired separation properties for membranes prepared from such fibrous supports.

The voids in the fibrous support can be of various sizes depending on the number and diameter of the nanofibers producing the void. As the diameter of the nanofibers making up a particular void increases, the size of the void decreases. However, the voids produced by either the symmetric or asymmetric arrangement of nanofibers of the present invention are interconnected. The size of the interconnected pores can be varied according to provide suitable flux, separation properties, and mechanical properties for membranes prepared from the fibrous support.

The nanofibers of the fibrous support of the present invention can be prepared from suitable polymers, including but not limited to polyolefins including polyethylene and polypropylene, as well as copolymers thereof; polysulfones such as aromatic polysulfones, polyethersulfones, etc.; halopolymers such as polyvinyl chloride, polyvinylidene chloride, polyvinylidene fluoride, etc.; polyesters such as polyethyleneterephthalate (PET), polytrimethylene terephthalate, polybutylene terephthalate, etc.; polyamides such as nylon 6, nylon 66, nylon 612, nylon 12, etc., aromatic polyamides; polycarbonates; polystyrenes; polyacrylonitriles; polyacrylates such as polymethylmethacrylate, copolymers of acrylic acid, methacrylic acid, hydroxyethylmethacrylate, etc.; polyacetates such as polyvinyl acetate and partially hydrolyzed polyvinyl acetates; polyalcohols such as polyvinyl alcohol, cationically modified polyvinylalcohol, anionically modified polyvinylalcohol; polysaccharides such as chitosan, hyaluronan, cellulose, regenerated cellulose, cellulose ethers such as methylcellulose, ethylcellulose, hydroxyethyl cellulose, cellulose esters such as cellulose acetates (including mono-, di-, and tri-acetates); proteins such as collagen, gelatin, etc.; ionomers; polyalkylene oxides such as polyethylene oxide, polypropylene oxide, polyethylene glycols, crosslinkable polyethylene glycol, etc.; polyurethanes; polyureas; poly(urethane-urea); polyimines such as polyethylene imine; polyvinylpyrrolidone; polyacrylic acids; polymethacrylic acids; polysiloxanes such as polydimethylsiloxane; poly(ester-co-glycol) copolymers; poly(ether-co-amide) copolymers; and mixtures, derivatives, copolymers and crosslinked forms of any of the above. Derivatives include ethers, esters, amides, etc. formed by alkylation, acylation etc. of functional groups (e.g., hydroxyl or amine groups), or by hydrolysis of hydrolyzable functional groups (e.g., esters, amides, anhydrides, etc.) present in the polymer of which the nanofiber is comprised. In particular embodiments, the nanofibers of the fibrous supports comprise polyacrylonitrile (PAN), polyethersulfone (PES), polyvinylidenefluoride (PVDF), crosslinked water-soluble polymers such as polyvinyl alcohol, polyvinylpyrrolidone, modified cellulose, modified chitosan, etc.

In some embodiments, the nanofibers of the fibrous support of the present invention comprise an uncrosslinked polymer, for example when the polymer is insoluble in any of the solvents which may be present in fluid medium contacting the fibrous support. However, in other applications, it may be desirable to prepare a fibrous support from polymers which are partially or completely soluble in solvents which may contact the fibrous support in use. In one embodiment, nanofibers comprising water soluble polymers such as polyvinyl alcohol, polysaccharides (e.g., chitosan and hyaluronan), polyalkylene oxides (e.g., polyethylene oxide), gelatin and derivatives can be cross-linked using methods known in the art. For example, polymers containing hydroxyl or amine groups (e.g., polyvinyl alcohols, polysaccharides, proteins, etc.) can be cross-linked using aldehydes (e.g., formaldehyde), dialdehydes (e.g., $C_2$-$C_8$ dialdehydes such as glutaraldehyde, glyoxal), mono-aldehydes having acid functionality (e.g., glyoxylic acid), polycarboxylic acids (e.g., oxydisuccinic acid, citric acid), etc. These compounds are capable of reacting with at least two hydroxyl (or amine) groups of a water-soluble polymer. Other crosslinking methods include thermal and radiation crosslinking methods (photo crosslinking, electron beam crosslinking, gamma crosslinking, etc.) of polymers optionally modified with, or mixed with, suitable cross-linking and radiation sensitizing agents/catalysts. Two important criteria for selection of cross-linking agent or method are that (1) the cross-linking agent or method should not dissolve the nanofibers, or (2) introduce large dimensional changes in the fibrous support (e.g., hydrophilic electro-spun nanofiber supports may display very large shrinking and hydrophobic solvents such as hydrocarbons because of their hydrophilic nature). In one embodiment, the nanofibers comprise polyvinyl alcohol crosslinked with glutaraldehyde. In other embodiments, the nanofibers comprise polyacrylonitrile, polysulfone, polyethersulfone, polyvinylidene fluoride, cellulose acetate, or polyvinyl alcohol.

In one embodiment of the present invention, the fibrous support described above can be a single layer, or comprise two or more layers. For example, the fibrous support can comprise a top layer and a bottom layer, wherein the top layer is disposed between the interfacially polymerized layer and the bottom layer. In other embodiments, the fibrous support can comprise three or more layers: a top layer, one or more middle layers, and a bottom layer, wherein the middle layers are disposed between the top and bottom layers. The top and bottom layers are continuously connected by the one or more middle layers (when present—otherwise the top and bottom layers are connected to each other), and all of the layers operate as a single unit.

The fibrous support ranges in thickness from about 1 µm to about 500 µm, in some embodiments about 3 µm to about 100 µm, and in other embodiments about 3 µm to about 50 µm. When the fibrous support comprises two or more layers, the top layer is typically about 1% to about 50% of the total thickness of the fibrous support, and the bottom layer is about 50% to about 90% of the total thickness of the fibrous support. In some embodiments, the top layer is about 10%, 15%, 20%, 25%, 30%, 35%, 40%, 45%, or 50% of the total thickness of the fibrous support, inclusive of all ranges and subranges between these values. When the fibrous support comprises a top layer, one or more middle layers, and the bottom layer, the top layer is typically about 20%, the middle layer(s) is/are about 50%, and the bottom layer is about 30% of the total thickness of the fibrous support.

Alternatively, the top layer of the fibrous support has an average thickness from about 2 nm to about 500 nm and the nanofibers have an average diameter of about 2 nm to about 500 nm, the bottom layer has an average thickness of about 500 nm to about 50 µm and the nanofibers of the bottom layer have an average diameter greater than about 500 nm. When present, the middle layer has a thickness ranging from about 2 nm to an average thickness of less than about 100 µm. The nanofibers of the middle portion have an average diameter of about 2 nm to about 2000 nm, in some embodiments about 10 nm to about 500 nm and in other embodiments about 100 nm to about 250 nm.

The diameter of the nanofibers in the top, middle (when present) and bottom layers of the fibrous support can vary discontinuously or continuously. For example, in a discontinuous arrangement the nanofibers of each layer can have the same average diameter, but the average diameter of the fibers in each layer is different. As a result, the average fiber diameter changes relatively abruptly from one layer to the next. In a continuous arrangement, the average fiber diameter of the various layers changes more or less continuously, such that the average fiber diameter increases smoothly through the thickness of the fibrous support. Typically, the nanofibers of the top layer of the fibrous support, which contact the interfacially polymerized polymer layer, have a smaller average fiber diameter compared to the fibers of the middle and bottom layers.

The interfacially polymerized polymer layer disposed on the surface of the fibrous support is prepared by interfacial polymerization methods in-situ on, partially within, or wholly within the top layer of the fibrous support. The interfacially polymerized polymer layer can have any composition which can be prepared by interfacial polymerization methods. For example, the interfacially polymerized polymer layer can comprise condensation polymers prepared by the reaction of at least one first polyfunctional monomer (e.g., polyalcohols and/or polyamines) dissolved in a first solvent (e.g., water or aqueous hydrophilic solvent systems) and at least one second polyfunctional monomer (e.g., a poly(acid halides) or other reactive "synthons" (i.e., synthetic equivalents) of carboxylic, sulfonic, or phosphonic acids, polyisocyanates, or combinations thereof) dissolved in second solvent which is substantially immiscible in the first solvent (e.g., hydrocarbon solvents such as hexane, hexanes, etc). "Substantially immiscible" solvents are those that have a solubility of less than about 1 wt. % in each other. Non-limiting examples of interfacially polymerized polymers include crosslinked aromatic polyamides, noncrosslinked aromatic polyamides, crosslinked non-aromatic polyamides, noncrosslinked non-aromatic polyamides, crosslinked poly (urea), crosslinked poly(urethane), crosslinked poly(urethane-urea), crosslinked poly(ethylene glycol), crosslinked polyimide, noncrosslinked polyimide, crosslinked polysulfone, noncrosslinked polysulfone, crosslinked polysulfonamides, uncrosslinked polysulfonamides, crosslinked sulfonated polysulfones, uncrosslinked sulfonated polysulfones, etc, and derivatives and combinations thereof. It will be recognized that any of the above polymer types can include other functional groups. So, for example, polyamides could include polymers containing functional groups such as ether, ester, sulfone, carboxylate (or carboxylic acid), hydroxyl, halogen, etc. Derivatives of the above polymer types include polymers chemically modified to include other functional groups, either by chemically modifying the monomers used to prepare the interfacial polymer prior to interfacial polymerization, or after interfacial polymerization. In addition, the crosslinked interfacial polymers can be crosslinked by reacting at least one trifunctional monomer (e.g., a tri-acid chloride such as trimesoyl chloride, a tri- or polyamine, a tri- or polyalcohol, etc.) during the interfacial polymerization; or alternatively can be crosslinked after completion of the interfacial polymerization using one or more of the crosslinking methods described herein.

In one embodiment, the interfacially polymerized polymers are prepared by reacting aromatic amines such as m-, p-, and/or o-phenylene diamine, cyclic diamines such as piperazine, Jeffamines® (di- and tri-amino polyoxyalkyleneamines available from Huntsman), 4,4'-bipiperidyl dihydrochloride, functionalized diamines such as 3,5-diamino benzenesulfonic acid and/or 3,5-diaminobenzoic acid, or combinations of these amines; with trifunctional acid chlorides such as trimesoyl chloride, difunctional acid chlorides such as terephthaloyl chloride, isoterephthaloyl chloride, etc., diisocyanates such as toluene diisocyanate, methylene diphenyldiisocyanate, hexamethylene diisocyanate, isophorone diisocyanate, and triisocyanates such as triphenylmethane triisocyanate (or combinations thereof).

The interfacially polymerized polymer layer can be formed on top of the nanofibers of the top layer, or may be integrated into at least a part of the top layer of the fibrous support, for example to improve the mechanical integrity of the interfacially polymerized polymer layer. The nanofibers of the top layer of the fibrous support can penetrate 1% to 100% (all the way through) the interfacially polymerized polymer layer. In some embodiments, the nanofibers penetrate 5%, 10%, 20%, 25%, 30%, 40%, 50%, 60%, 70%, 80%, 90%, or about 100% of the total thickness of the interfacially polymerized polymer layer, inclusive of all values and subranges therebetween. When the nanofibers of the top layer penetrate into the interfacially polymerized polymer layer, the portion of the interfacially polymerized polymer layer containing nanofibers can be termed a "nanocomposite layer", since the interpenetrating nanofibers form a composite structure with the interfacially polymerized polymer layer. In other words, the interfacially polymerized polymer layer can sit on top of the top surface of the fibrous support, or can be interpenetrated to any degree by the nanofibers of the top layer of the fibrous support The interfacially polymerized polymer layer is formed by impregnating the fibrous support with a first solution comprising the first solvent and at least one "first" polyfunctional monomer, e.g. an aqueous solution of one or more polyamines as described herein and/or one or more polyols as disclosed herein. If needed, excess first solution can be drained or otherwise removed from the fibrous support. A second solution, comprising the second solvent (which is immiscible in the first solvent) and at least one "second" polyfunctional monomer (e.g., trimesoyl chloride in hexane), reactive with the "first" polyfunctional monomer of the first solution, is then deposited on the top surface of the fibrous support. The polyfunctional monomers of the first and second solution then react at the interface of the two immiscible solutions, either on, partially within, or wholly within the top surface of the fibrous support. The position of the interfacially polymerized polymer layer—either on or in the top surface of the fiber support—can be adjusted appropriately by the amount of first solution added to the fibrous support, or the amount of first solution drained from the fibrous support, thereby adjusting the position of the resulting interface between the first and second solutions within the fibrous support during the interfacial polymerization.

Any suitable means for depositing the first and second solutions onto the fibrous support may be used. For example, the fibrous support can be impregnated with the first solution by dipping into a bath comprising the first solvent and first polyfunctional monomer, or by spraying the fibrous support with a solution of the first solvent and first polyfunctional monomer. Excess first solution can be removed by any suitable means (e.g. by simply draining off excess solution, or using nip rolls, etc.). The second solution can then be applied similarly by dip coating or spraying. After allowing the reaction to proceed for a suitable time period, the fibrous support, now coated on one surface with an interfacially polymerized polymer layer, can be drained of excess monomer, washed, and dried as needed.

The interfacially polymerized polymer layer can further comprise at least one hydrophilic or hydrophobic nanoparticulate filler. Non-limiting examples of suitable hydrophilic nanoparticulate fillers include oxidized carbonaceous nanoparticles, surface grafted carbonaceous nanoparticles, water dispersible nanoclays, and combinations thereof. Carbonaceous nanoparticles can include single-walled carbon nanotubes, multi-walled carbon nanotubes, carbon nanofibers, buckyballs (also known as fullerene $C_{60}$ and/or Buckminster fullerene), graphene sheets, graphite nanoparticles, etc, which are surface grafted or surface oxidized by various known methods, including oxidation by treatment with suitable oxidizing agents such as ozone, halogenation by treatment with halogens or halogenating agents, hydrogenation, thiolation, esterification, reaction with hydrophilic radicals, reaction with hydrophilic carbenes, nitrenes, etc. In some embodiments, a hydrophilic or water-soluble polymer or oligomer is grafted to the carbonaceous nanoparticles surface. Water dispersible nanoclays include e.g., smectite clays such as montmorillonite and lucentite.

In another embodiment, the nanoparticulate filler can include metal nanoparticles or inorganic nanotubes which may contain metallic components including, but not limited to, gold, cobalt, cadmium, copper, iron, lead, zinc, and palladium, as well as silicate based nanoparticles such as silica, polyhedral oligomeric silsesquioxanes, layered silicates, and derivatives thereof.

In one embodiment, the nanoparticulate filler may be functionalized with at least one hydrophilic functional group including, but not limited to, carboxylic acid groups, carbonyl groups, hydroxy groups, ethylene oxides, alcohols, saccharides and amine groups or supramolecular complexes including DNA molecules, DNA fragments, and protein fragments. Suitable DNA molecules may include those obtained from plants, animals and human, sources being, in some embodiments, from about 1 to about 1000 nucleotides in length, in embodiments from about 10 to about 100 nucleotides in length.

Non-limiting examples of suitable hydrophobic nanoparticulate fillers include carbonaceous nanoparticles, surface functionalized carbonaceous nanoparticles, nano-organoclays, polyhedral oligomeric silsesquioxane cage molecules (e.g., POSS), etc. the hydrophobic carbonaceous nanoparticles can include single-walled carbon nanotubes, multi-walled carbon nanotubes, carbon nanofibers, buckyballs, graphene sheets, graphite nanoparticles, etc. These carbonaceous nanoparticles can be unmodified (if the surface properties are inherently hydrophobic), or further surface-modified to provide hydrophobic properties. For example, the carbonaceous nanoparticles can be reacted with hydrophobic radicals or other reactive species. Nano-organoclays are typically smectite clays (e.g., montmorillonite or lucentite clays modified with hydrophobic amines or quaternary amines (e.g., Nanomer® clays from Nanocor).

In other embodiments, the nanoparticulate filler may be functionalized with at least one hydrophobic functional group including, but not limited to, aliphatic compounds including linear molecules containing hydrocarbons having from about 1 to about 20 carbon atoms, e.g., octadecylamine (ODA)), polypropylene-graft-maleic anhydride oligomers (including one having a $M_n$ of about 3,900 g/mol, a Mw of about 9,100 g/mol, and an acid number of about 47 mg KOH), fluorinated compounds, including 3-(perfluorooctyl)propylamine and the like), and aromatic compounds including aromatic hydrocarbons, e.g. alkylidenediamines such as hexamethylenediamine and the like.

Hydrophobic or hydrophilic nanofiber nanoparticulate fillers, such as modified multiwalled carbon nanotubes, provide additional interconnected (e.g. because the nanofibers are interconnected) molecular channels. These additional interconnected molecular channels increase the permeability of the interfacially polymerized polymer layer. In a particular embodiment, the nanofiber nanoparticulate fillers are hydrophilic.

In yet another embodiment, the interfacially polymerized polymer layer can further comprise functionalized molecules. Functionalized molecules include organic or inorganic hydrophobic molecules; hydrophilic molecules such as polyethylene glycols (e.g., glycerol); organic-inorganic polymer composites include POSS, antibodies, antigens, DNA, RNA, proteins, peptides, and combinations of any of the above.

The nanoparticulate filler may have varying morphologies, from essentially rod-like or cylindrical (e.g., nanofibers), to essentially spherical, (e.g., buckyballs having a soccer ball type configuration combining pentagons and hexagons). Thus, in some embodiments, the diameter of a nanoparticulate filler may be from about 0.3 nm to about 300 nm, in some embodiments from about 0.5 nm to about 50 nm, in other embodiments from about 1 nm to about 30 nm. Where the nanoparticulate filler is rod-like or cylindrical in shape, it may have a length of from about 1 nm to about 500 µm, in some embodiments from about 100 nm to about 50 µm, typically from about 500 nm to about 5 µm. Where the nanoparticulate filler is a carbon nanotube, such as a single-walled carbon nanotube, a multi-walled carbon nanotube, and/or a carbon nanofiber, the diameter of such a nanotube may be from about 1 nm to about 300 nm, in some embodiments about 5 nm to about 200 nm, in other embodiments about 10 nm to about 100 nm.

The nanoparticulate filler may be present in the interfacially polymerized polymer layer in an amount of from about 0.1% by weight to about 95% by weight of the coating, in some embodiments from about 0.2% by weight to about 30% by weight of the coating, in other embodiments from about 0.5% by weight to about 20% by weight of the coating. Conversely, the interfacially polymerized polymer can comprise from about 5 to about 99.9% by weight of the interfacially polymerized polymer layer, in some embodiments from about 70% by weight to about 99.8% by weight of the coating, typically from about 80% by weight to about 99.5% by weight of the interfacially polymerized polymer layer. The incorporation of functionalized nanoparticulate filler in the coating layer can improve the mechanical strength of the coating layer, and also increase the fluid permeability of the coating layer (e.g., a hydrophilic nanoparticulate filler can increase the water permeability of the interfacially polymerized polymer layer by providing a hydrophilic channel through the layer. For example, interfacially polymerized polymer layers having modified carbon nanotubes as the functionalized nanoparticulate filler in an amount from about 1% by weight to about 10% by weight can, in certain embodiments, be from about 50% to about 300% stronger in toughness (the toughness was estimated by the area under the stress-strain curve) compared to interfacially polymerized polymer layers without the nanoparticulate fillers, and may exhibit an increase in flux rate (with the same rejection rate) that is from about 50% to about 1000% greater than interfacially polymerized polymer layers without the nanoparticulate fillers.

The interfacially polymerized layer can contain a single type of nanoparticulate filler, metal or inorganic nanoparticle, or functionalized molecule, or combinations of different types of nanoparticulate fillers and/or metal or inorganic nanoparticles, and/or functional molecules.

In other embodiments, the article of the present invention comprises a fiber support comprising nanofibers, an interfacially polymerized polymer layer disposed on the surface of the fibrous support, and a substrate layer disposed on the opposing surface of the fibrous support, such that the fibrous support is disposed between the interfacially polymerized polymer layer and the substrate layer. The substrate layer is typically a porous layer, for example a woven or non-woven fabric. In one embodiment, the substrate layer is a non-woven fabric comprising inorganic or organic polymeric fibers, for example polyester fibers, e.g. comprising poly(ethylene terephthalate); polyolefin fibers, e.g. comprising polypropylene; cellulosic fibers, e.g. comprising cellulose or cellulose acetate; polyamide fibers; poly(urethane) fibers; glass or mineral fibers; inorganic fibers (e.g., ceramic fibers, metallic fibers, and mixtures thereof. The non-woven substrate layer can have an average thickness from about 20 μm to 20 mm. One function of the non-woven matrix is to provide additional support to the symmetric or asymmetric arrangement of the fibrous supports disclosed herein.

The articles of the present invention can be used as protective materials, clothing, biological substrates (e.g. scaffolds for tissue regeneration, immobilized enzymes and catalyst systems, wound dressing articles, artificial blood vessels and materials for the prevention of post-operative induced adhesions), optical and chemical sensors, fluid separation membranes, e.g. ultrafiltration membranes, nanofiltration membranes, reverse osmosis membranes, and forward osmosis membranes, as well as electrical conductors. In one embodiment, the articles of the present invention are membranes. In a particular embodiment, the articles of the present invention are reverse osmosis membranes.

The fibrous support comprising nanofibers may be prepared by any suitable method of manufacturing nanofibers. The fiber support can be prepared using electro-spinning, electro-blowing, blowing-assisted electro-spinning, and/or solution blowing or casting technologies. Blowing-assisted electro-spinning and electro-blowing both use electric force and gas-blowing shear forces. In blowing-assisted electro-spinning processes, the electric force is the dominating factor, while the gas-blowing feature can assist in shearing the fluid jet stream and in controlled evaporation of the solvent (lower throughput, smaller diameter). In contrast, in electro-blowing processes the gas-blowing force is the dominating factor to achieve the desired spin-draw ratio, while the electric force may enable further elongation of fiber (higher throughput, larger diameter). Electro-spinning processes use only electric force, but without the assistance of gas flow, while solution blowing processes use only gas flow, without the use of electric force. In one particularly useful embodiment, the middle layer, such as PAN or PVA, may be electrospun on a substrate, such as a non-woven PET micro-filter (FO2413 from Freudenburg Nonwovens) utilizing methods known to those skilled in the art.

The applied electric field potentials utilized in electro-spinning can vary from about 10 to about 40 kV, typically from about 15 to about 30 kV, with a distance between the spinneret and the collector of from about 5 to about 20 cm, typically from about 8 to about 12 cm, and a solution flow rate of from about 10 to about 40 μL/min, typically from about 20 to about 30 μL/min. In one embodiment the electro-spinning process can use an applied electric field strength of about 2 kV/cm and a solution flow rate of about 25 μL/min.

Methods for forming fibers by electro-blowing are within the purview of those skilled in the art and include, for example, the methods disclosed in (e.g., the method described in U.S. Published Patent Application No. 2005/0073075, herein incorporated by reference in its entirety for all purposes). Briefly, in an electro-blowing process, an electrostatic field is combined with a gaseous flow field. Like melt blowing (no charge required), where the liquid droplet is pulled out by the gaseous flow, with electro-blowing the combined forces are strong enough to overcome the surface tension of the charged liquid droplet. This permits the use of electrostatic fields and gas flow rates that are significantly reduced compared to either method alone. Both the gaseous flow stream and the electrostatic field are designed to draw the fluid jet stream very fast to the ground. The spin-draw ratio depends on many variables, such as the charge density of the fluid, the fluid viscosity, the gaseous flow rate and the electrostatic potential. In some embodiments, these variables can be altered in mid-stream during processing. For example, injection of electrostatic charges can be used to increase the charge density of the fluid or even convert a neutral fluid to a charged fluid. The temperature of the gaseous flow can also change the viscosity of the fluid. The draw forces increase with increasing gaseous flow rate and applied electrostatic potential. The intimate contact between the gas and the charged fluid jet stream provides more effective heat transfer than that of an electro-spinning process where the jet stream merely passes through the air surrounding the jet stream. Thus, the gas temperature, the gas flow rate, and the gaseous streaming profile can affect and control the evaporation rate of the solvent if the fluid is a solution. The gas temperature can vary from liquid nitrogen temperature to superheated gas at many hundreds of degrees; the preferred range depends on the desired evaporation rate for the solvent and consequently on the solvent boiling temperature. The streaming profiles are aimed at stabilizing the jet streams and should be similar to those used in melt blowing.

In electro-blowing embodiments, the feeding rate of the polymer solution per spinneret for forming the fibrous support may be from about 5 to about 2500 μL/min, typically from about 20 to about 300 μL/min, in embodiments from about 35 to about 150 μL/min. The air blow temperature may be from about 0° C. to about 200° C., typically from about 20° C. to about 120° C., in embodiments from about 25° C. to about 90° C. The air blow rate per spinneret may vary from about 0 standard cubic feet per hour (SCFH) to about 300 SCFH, typically from about 5 SCFH to about 250 SCFH, in embodiments from about 20 SCFH to about 150 SCFH. The electric potential can be from about 1 kV to about 55 kV, typically from about 15 kV to about 50 kV, in embodiments from about 30 kV to about 40 kV, with a typical spinneret to collector distance of about 10 cm.

Where the nanofibrous scaffold is formed by blow-assisted electrospinning, the feeding rate of the polymer solution per spinneret for forming the nanofibrous scaffold may be from about 5 to about 150 μL/min, typically from about 10 to about 80 μL/min, in embodiments from about 20 to about 50 μL/min. The air blow temperature may be from about 0° C. to about 200° C., typically from about 20° C. to about 120° C., in embodiments from about 25° C. to about 90° C. The air blow rate per spinneret may vary from about 0 standard cubic feet per hour (SCFH) to about 300 SCFH, typically from about 5 SCFH to about 250 SCFH, in embodiments from about 20 SCFH to about 150 SCFH. The electric potential can be from about 1 kV to about 55 kV, typically from about 15 kV to about 50 kV, over a typical in embodiments from about 20 kV to about 40 kV, with a typical spinneret to collector distance of about 10 cm.

In other embodiments, fibrous supports may be formed by solution blowing, which is similar to melt blowing except a polymer solution instead of a polymer melt is used to fabricate the scaffolds. Such techniques are within the purview of those skilled in the art and include the formation of a polymeric material and blowing agent in a single phase, typically a liquid, which is then sprayed utilizing conventional equipment similar to that utilized in electro-blowing, except that an electrical field is not utilized in spraying the liquid. Parameters useful for solution blowing include, for example, the use of very high shear forces obtained by using gas flow at speeds from about one hundredth of the speed of sound to near the speed of sound in air, i.e., about 600 miles per hour.

The fibrous support of the present invention is similar to non-woven supports prepared by e.g., melt-blowing, except with fiber diameters in the sub-micron size range, of the order of about 10 to about 5,000 times smaller in diameter compared with melt-blown substrates. The smaller pore sizes of these electro-spun non-woven supports, and the inter-connected void volume which these supports possess, can be used as a scaffold to support a thinner selective coating layer, e.g., for UF, NF, RO, and forward osmosis membranes, with much improved throughput.

The selective coating layer by interfacial polymerization can be easily applied to electrospun nanofibrous membranes for the following reasons: (1) easy wet-ability and good liquid retention property of fibrous support, and (2) easy prevention of the pore blockage due to the highly interconnected pore structure (easy washability). In addition to the easiness of coating process, the combination of nanofiber and interfacially polymerized ultra-thin coating has several unique features over the conventional thin film composite membranes: (i) proper nanofiber modifications (either surface or composite approach (nanocomposite or blend)) can enhance the membrane selectivity and adhesion to the top coating layer; (ii) flux enhancing permeable water nanochannels can be incorporated into the interfacially polymerized polymer layer by incorporating surface modified nanofillers (e.g. carbon nanofibers/nanotubes or the nanofibers of the fibrous support themselves) in the interfacial polymerization process; (iii) the molecular cavity and functionality (e.g. hydrophilicity) of the top layer can be fined-tuned by proper selection of a wide range of monomers for interfacial polymerization on fibrous supports comprising nanofibers; (iv) the highly porous interconnected structure of the fibrous support leads to significantly lower resistance of the flow and higher flux rate compared to conventional microporous support-based thin film composite membranes. For example, nanofibers of the top layer of the fibrous support which interpenetrate the interfacially polymerized polymer layer can function as "conduits" which increate the permeate flux of membranes comprising the articles of the present invention. In addition, the interfacially polymerized polymer layer is mechanically supported by the interpenetration of nanofibers from the fibrous support.

Articles comprising fibrous supports are used for clothing, insulation, as enzyme supports, for biomedical applications, and for gas and liquid filtration systems. Nanofibrous supports comprised of nanofibers can be arranged to form nanofibrous webs (i.e., sheets) having high surface area, a range of pore sizes, and large void volumes (e.g., >60%) as well as other useful properties.

When used as liquid separation membranes, the articles of the present invention can be used in any suitable configuration, for example as tubular, hollow fiber or flat sheet membranes, incorporated into conventional membrane module configurations known in the field of membrane separations. For example, in one embodiment, the articles of the present invention can be flat sheet liquid separation membranes configured in a spiral wound membrane module or a flat sheet membrane module. In such configurations, the membranes can, as needed, be sandwiched between the appropriate spacers inside of a pressure housing. One or more membranes may be incorporated into each membrane module, and one or more modules can be interconnected with the appropriate piping, pumps, etc. known in the art to provide a fluid separation system capable of carrying out separations in fluid mixtures.

The present invention is described in greater detail in the sections below.

EXAMPLES

Electrospun fibrous supports of PAN (polyacrylonitrile) are useful for membrane applications for two reasons: (1) PAN has been widely used for ultrafiltration (UF), nanofiltration (NF), and reverse osmosis (RO) due to its good solvent resistance; and (2) PAN has also been electrospun into precursor form for the fabrication of carbon nanofibers, where the electrospun fiber diameter has been shown to vary from hundreds of nanometers to several micrometers.

Chitosan is a hydrophilic biopolymer. It is insoluble in neutral pH conditions and thus is water-resistant but water-permeable. It has been used for anti-fouling enhancement of filtration membranes. A schematic diagram of three-tier composite membranes is illustrated in FIG. 1, containing a 'non-porous' hydrophilic coating that is water permeable (chitosan), an electrospun nanofibrous support (PAN) and a non-woven microfibrous substrate (PET). Although the schematic diagram of FIG. 1 shows a third non-woven support, as stated above this layer is optional and may only be used for additional support when conditions so dictate.

The following examples with reference to FIGS. 2-17 are used to illustrate the present invention.

Example 1

Top Layer Prepared by Chitosan Solution Casting

Materials and Preparation

Polyacrylonitrile (PAN) with a weight-average molecular weight ($M_w$) of about $1.5 \times 10^5$ g/mol and chitosan with a viscosity-based molecular weight ($M_v$) ranging between $1.9 \times 10^5$ and $3.1 \times 10^5$ g/mol were purchased from the Aldrich Chemicals. Dimethylformamide (DMF, Aldrich) and acetic acid (glacial, Fischer) were used as solvents for PAN and chitosan, respectively, without further purification. The poly (ethylene terephathalate) non-woven substrate (PET microfilter FO2413 with an average fiber diameter of about 10 mm) for membrane support was kindly provided by Freudenberg Nonwovens (Hopkinsville, Ky.).

PAN was dissolved in DMF at 50° C. and the solution was stirred for about one day, or until the solution became homogenous. Polymer solutions of several different concentrations were prepared, ranging from 4 to 12 wt %. Chitosan was purified before use by the following procedure. The chitosan sample (~1 g) was dissolved in acetic acid (1 wt %) and the solution was filtered using a nonporous medium sintered glass filter to remove insolubles. The chitosan solution was subsequently cast in a plastic petri dish and left in a fumehood to dry. The dried chitosan film was then soaked in sodium hydroxide solution (concentration: 1 M) for a few hours. After being peeled off of the petri dish, the chitosan films were washed with de-ionized water until neutralized. The neutralized films were freeze-dried for 24 h before use. Coating solutions of the purified chitosan were prepared at a concentration range from 0.5 to 1.2 wt % in acetic acid solution (1 wt %). The solution pH was adjusted to 6.5 by 1 N sodium hydroxide.

Fabrication of Three-Tier Composite Membrane

A non-woven PET micro-filter substrate was first primed with a 1 wt % chitosan solution to enhance its adhesion with electrospun PAN nanofibers. In this process, about 2 mL of chitosan solution was used to prime the sample with $7.6\times10^2$ cm$^2$ cross-section area (the total amount of pre-coated chitosan was about 20 mg). The PAN solution (4-12 wt % in DMF) was electrospun directly onto the surface-coated PET nonwoven substrate at 14-20 kV. The flow rate was 10-20 mL/min and the spinneret diameter was 0.7 mm. The distance between the collector (PET substrate) and the spinneret was 10-18 cm, depending on the polymer concentration. In the electrospinning setup, a rotating metal drum with the diameter of about 9 cm and a rotating speed of about 300 rpm was used to collect the deposited nanofibers. A stepping motor was used to control the oscillatory translational motion perpendicular to the drum rotation direction (the oscillation distance was about 12 cm) to ensure the production of uniform electrospun supports with sufficient membrane area (i.e. larger than $7.6\times10^2$ cm$^2$). The typical amount of PAN nanofibers spun per unit area was about 1.2 mg/cm$^2$. In addition to electrospinning of a solution at a fixed polymer concentration, the following procedure was also used to fabricate asymmetric scaffolds consisting of two multi-layers of fibers having different fiber diameters. The first multi-layer was produced by using a 10 wt % or higher polymer concentration solution, resulting in a larger fiber diameter; the second multi-layer was produced by using a 4 wt % solution, resulting in a smaller fiber diameter. The finer and denser fibrous structure on top was designed to support a thinner layer of coating that could withstand the expected operating pressure of the filtration process.

The coating layer was applied onto the fibrous composite support containing electrospun PAN scaffold and non-woven PET substrate by cast-coating with a chitosan solution (concentration: 0.5-1.4 wt %, pH 6.5). To ensure the creation of a relatively smooth chitosan layer on the surface of PAN scaffold, the following procedure was used. The scaffold was first soaked in 1 N NaOH solution before coating to minimize the penetration of chitosan solution into the PAN fibrous support. The resulting three-tier composite membrane was dried for one day under ambient conditions. The dried membrane was then washed with water until the membrane became completely neutralized. The total thickness of chitosan/PAN layer (excluding the non-woven PET substrate) was about 60 μm after drying.

Characterization

The structures of the top-layer coating, the electrospun mid-layer support and the cross-section of the coating/nanofibrous support interface were examined by scanning electron microscopy (SEM, LEO 1550) equipped with Schottky field emission gun (10 kV) and Robinson backscatter detector. All specimens received 24 s of gold coating to minimize the charging effect. The fiber diameter and pore area were measured by a Scion® image analysis program after calibration with standards. The feed solution was prepared by mixing of vegetable oil (1350 ppm), surfactant (150 ppm, Dow Corning 193 fluid) and deionized water. A custom-built cross-flow filtration cell (active filtration area: 0.00652 m$^2$) was used to test the filtration performance of composite membranes. The chosen trans-membrane pressure (Δp) was 50 psi and the chosen inlet pressure was 130 psi, which was maintained constant throughout the entire experiment. The chosen operating temperatures were 30-33° C. The flux measurements were repeated three times to confirm the performance of each sample.

The filtration efficiency of the composite membrane was determined as follows. The surfactant concentrations of the initial feed solution and the filtered liquid (permeate) were determined by ultraviolet-visible (UV) spectroscopy (Bio-Rad SmartSpec 3000) at a wavelength of 230 nm (i.e. in the range of 150-0 ppm oil-surfactant mixture). The rejection percent was calculated by using the following equation.

$$\text{Rejection (\%)} = \frac{(C_f - C_p)}{C_f} \times 100 \qquad \text{Eq. (1)}$$

where $C_f$ and $C_p$ represent the surfactant concentration of the feed solution and that of the permeate, respectively.

Electrospinning of PAN Nanofibrous Support

Figure 2:
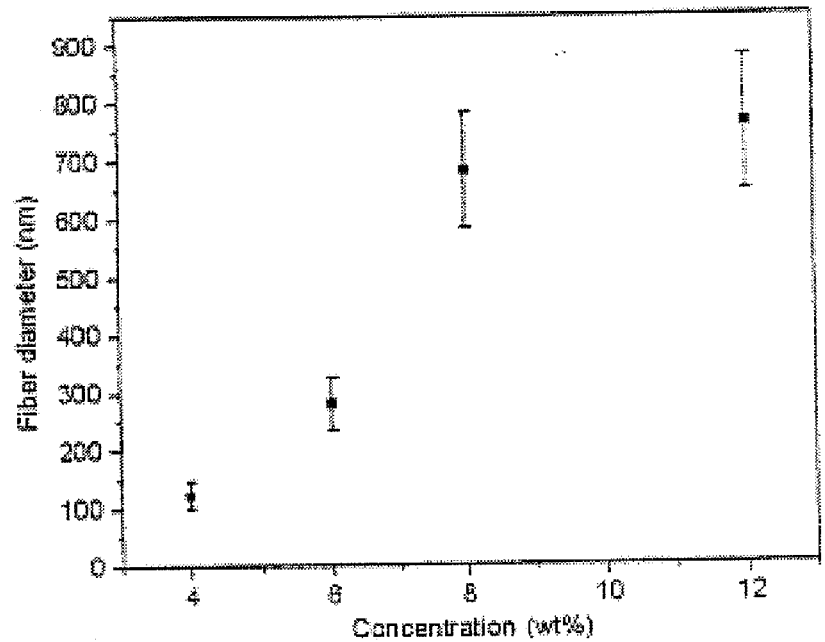
FIG. 2 illustrates changes in electrospun PAN fiber diameter with polymer solution concentration (4-12 wt %).
Figure 3:
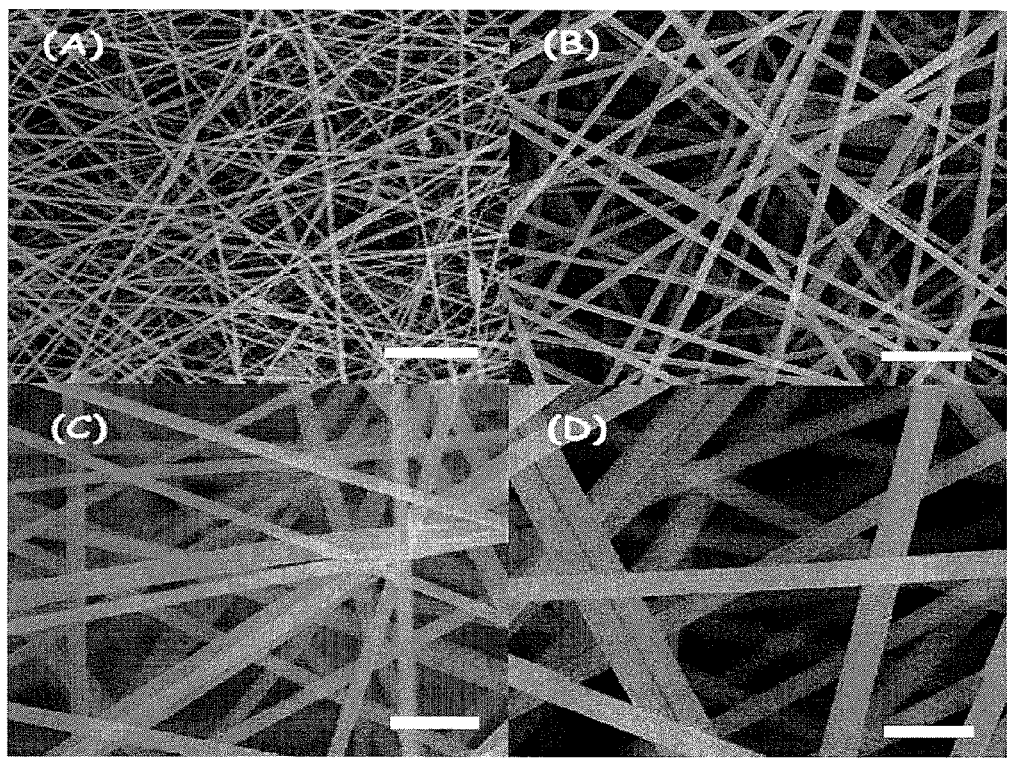
FIG. 3 shows corresponding SEM images of PAN fibers electrospun at different concentrations.

There are many parameters in electrospinning (e.g. flow rate, applied electric field, and distance between spinneret and collecting drum) that can be used to control the fiber diameter. One of the more effective methods of altering the fiber diameter was to change the polymer solution concentration used to spin the fibers. By changing the PAN concentration from 4 to 12 wt % while keeping other processing parameters constant, the average fiber diameter could be varied from 124 nm to 720 nm, as shown in FIG. 2. Furthermore, the fiber diameters at higher concentrations (i.e. more than 10 wt %) appeared to approach a constant value (~750 nm) under our experimental conditions. FIG. 3 shows the corresponding SEM images of PAN fibers electrospun at different concentrations, clearly illustrating that all the fabricated fibers showed fairly good uniformity. The average diameter was found to increase with the solution concentration.

Surface Porosity of Electrospun Support

Figure 4:
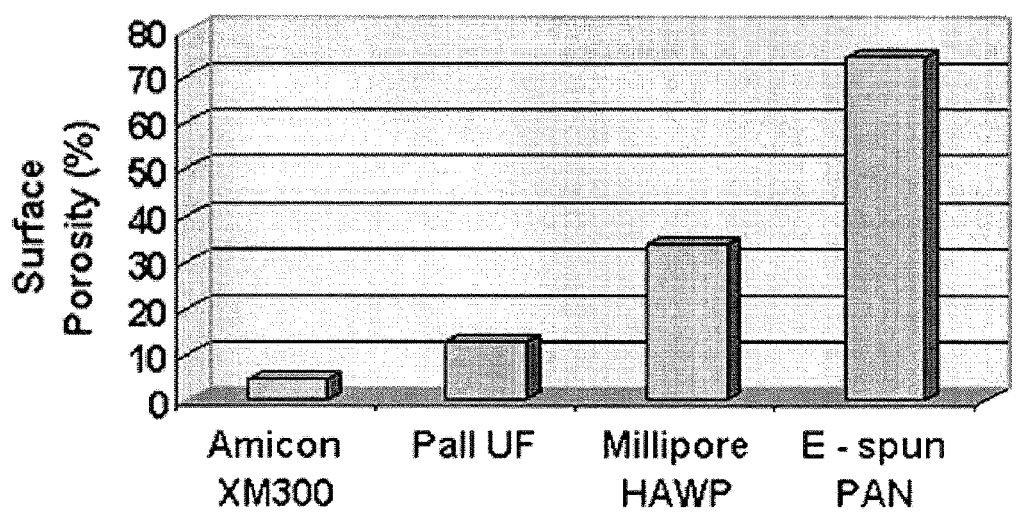
FIG. 4 shows the results of commercial image analysis software used to determine surface porosity of electrospun membranes.

Commercial image analysis software was used to determine the surface porosity of electrospun supports as well as those of commercial UF/NF filters. The results are shown in FIG. 4. The electrospun support based on the 4 wt % of PAN solution exhibited the highest porosity value (~73%), which was significantly higher than the values determined from commercial UF (e.g. Pall Corporation) and NF (e.g. Amicon XM300) filters and more than 2 times larger than that of Millipore HAWP microfiltration filter (~34%).

Figure 5:
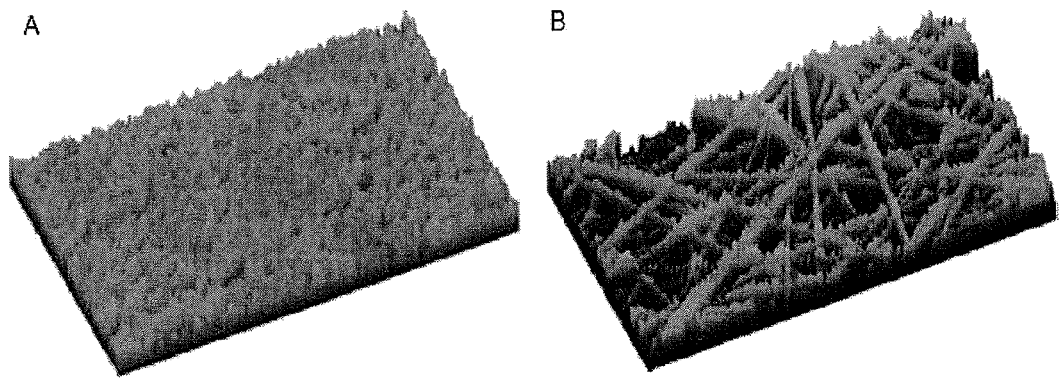
FIG. 5 shows surface plots for (A) Pall UF membrane and (B) 4 wt % PAN electro-spun membrane.

The different nature of surface porosity between a conventional ultrafiltration filter (e.g. an UF filter from Pall Corporation) based on the porous membrane format and the electrospun support of the present invention can be clearly seen from the tilted view of processed image by the image analysis program (FIG. 5). It is noted that while the surface porosities in UF and NF filters are quite similar, they are very different from the bulk porosity. In FIG. 5, the processed surface SEM images exhibited the surface structure of the dense top layer resulting from the solvent evaporation process near the membrane surface during the phase inversion procedure. However, the surface porosity of an electrospun PAN support was found to be very close to its bulk porosity. The porosity appeared to be related mainly to the fiber diameter. The SEM images showed that variations in the fiber diameter could change the porosity under our experimental conditions. Assuming that the pore geometry could be described by the Hagen-Poiseuille model and the surface porosity of the membrane was close to its bulk porosity, then the surface porosity could be correlated to the flux by using the following equation.

$$J_w = r_p^2 \frac{\Delta P}{8\mu(\Delta x 1 A k)} \qquad \text{Eq. (2)}$$

where $J_w$ represents the flux (m/s), $r_p$ represents the effective pore radius (m), ΔP represents the applied pressure drop. (kN/m$^2$), μ is the viscosity of solution (Pa s), Δx is the effective membrane thickness (m) and $A_k$ is the porosity of the membrane. Here, the flux is taken to be proportional to the surface porosity. For practical oily water ultrafiltration, a more complex expression with additional parameters should be used. However, Eq. (2) provides a simple guideline to correlate the flux performance with surface porosity. It also illustrates that the electrospun nanofibrous scaffold should have a much higher flux than conventional nonporous membranes in UF or NF filters.

Three-Tier Composite Membranes for Ultrafiltration

Although electrospun scaffolds can be considered as effective filters for liquid filtration, there is a major drawback for practical use of these materials by themselves, i.e. the high surface porosity of the electrospun nanofibrous scaffold will lead to a high-fouling problem. The symptom of fouling is an unavoidable consequence of gradual blockage of permeation in the membrane during filtration. The fouling rate is a function of many variables (e.g. the surface characteristics of the membrane, the surface-to-volume ratio of the membrane, the flow rate, the permanent concentration, the filtration temperature, the character of feed and reentrant streams), where the surface characteristics play a major role. The high fouling rate indicates that the replacement frequency must be high, resulting in an effective correspondingly higher operational cost. A thin layer of hydrophilic but water resistant, nonporous, but water permeable, chitosan coating was deposited onto the nanofibrous PAN surface to minimize the fouling concern. The chitosan coating would allow water to penetrate without losing too much flow rate, while the smooth coating surface would minimize the blockage problem. Moreover, in order to support a uniform chitosan coating, an asymmetric structure of nanofibrous support that had two multi-layers of different fiber diameters was constructed. The asymmetric structure possesses: (1) a multi-layer of finer fiber diameter with lower porosity to support the coating, (2) a multi-layer of larger fiber diameter with higher porosity to interface the transition with the non-woven PET substrate.

Figure 6:
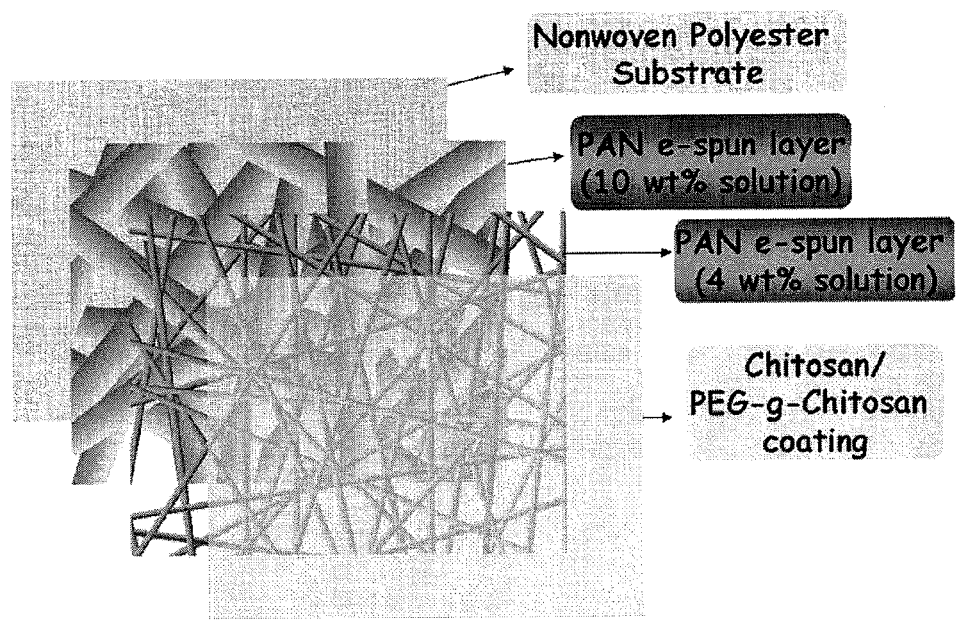
FIG. 6 shows a schematic diagram for the assembly of a three-tier composite membrane.
Figure 7:
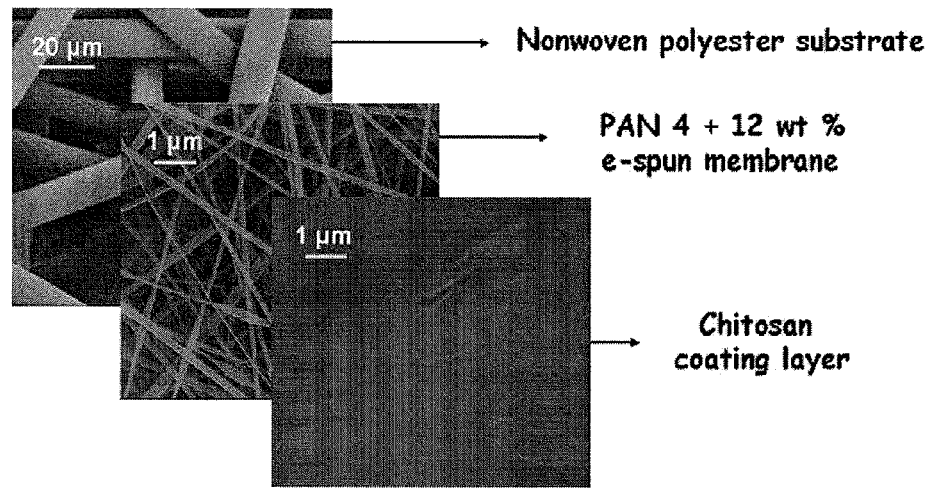
FIG. 7 shows SEM images of each layer in a three-tier composite membrane for ultrafiltration.
Figure 8:
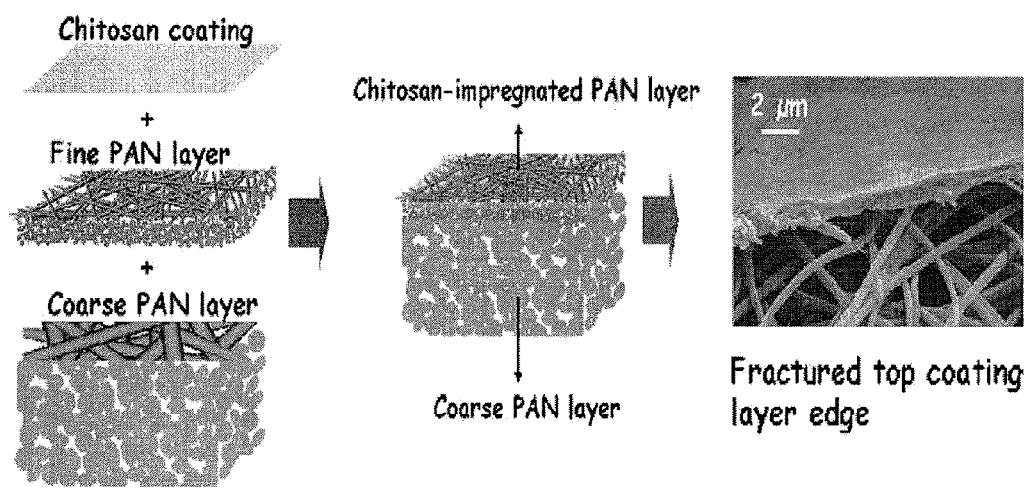
FIG. 8 shows the fabrication schematics of an electrospun scaffold with a coating layer.

It is known that the volumetric flow rate is inversely proportional to the thickness of nonporous top coating layer, which obeys D'Arcy's law $$J=KP/(\eta L) \qquad \text{Eq. (3)}$$

where K is the hydraulic permeability of the membrane, h is the viscosity of the liquid, L is the thickness of the membrane and P is the pressure. Thus, the thinner the coating layer, the higher the flux. In order to apply a thin coating layer on top of the electrospun scaffold, finer fiber diameter and denser structure could better maintain the coating surface uniformity. Based on experimental results from electrospinning of varying PAN solutions, the scaffold generated by the 4 wt % solution was found to have the smallest fiber diameter (FIGS. 2 and 3). A three-tire composite membrane having an asymmetric nanofibrous PAN support is illustrated in FIG. 6, where the asymmetric support was fabricated by sequential electrospinning of 12 and 4 wt % solutions, respectively. The thickness of the scaffold produced by the 4 wt % solution was estimated to be the order of micrometers from the cross-section SEM image of composite membrane. Even with the pre-rinsing procedure (using 1 N NaOH solution), the chitosan coating layer could still penetrate into several nanofibers (with a mean diameter of about 124 nm). FIG. 7 shows SEM images of the surfaces of each layer: non-woven PET substrate, electrospun asymmetric PAN scaffold (from sequential process of 12 and 4 wt % solutions) and chitosan coating layer. Schematic diagrams of the cross-sectional assembly and a typical SEM image of fractured cross-sectional view of the assembled membrane are shown in FIG. 8. From SEM observations, the surface of the chitosan coating layer seemed to be smooth and flat, and the coating thickness was about 1 mm. With different chitosan concentrations, the thickness of the coating layer could be changed from 1 mm to 3 mm.

Evaluation of Filtration Performance

Figure 9:
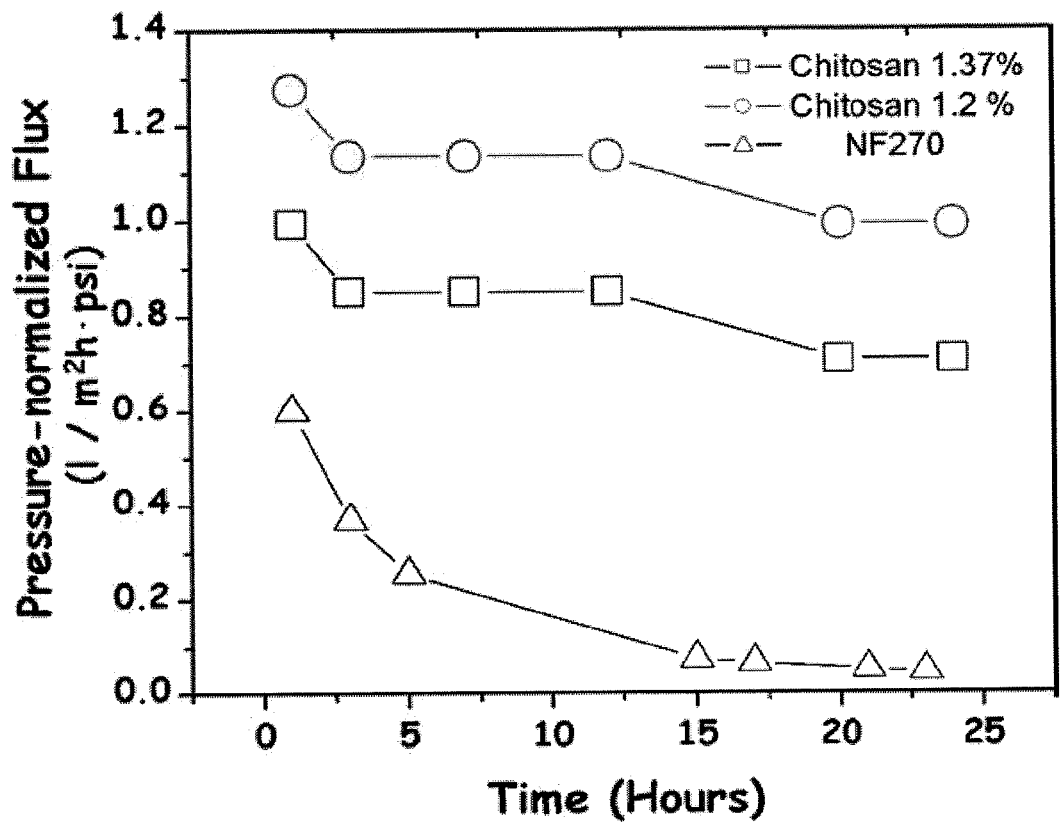
FIG. 9 graphically shows the flux performance of a three-tier composite with coating of chitosan solutions on an asymmetric electrospun PAN support, as well as an NF filter for filtration of oily wastewater.

Based on the cross-flow ultrafiltration measurement, chitosan/PAN/PET three-tier composite membranes showed much higher average flux rates than commercial UF and NF filters. A comparison among two composite membranes with different chitosan coating thicknesses (one about 1.3 μm by coating of 1.37 wt % solution and one about 1 μm by coating of 1.2 wt % solution) and a commercial NF fiber (i.e. NF 270 from Dow) was made, and the results are shown in FIG. 9. Both chitosan/PAN/PET three-tier composite membranes exhibited an order of magnitude higher flux rate than the chosen NF filter after 20 h of operation, and the membrane with the thinnest chitosan layer exhibited a higher flux rate. A thickness reduction of about 0.5 μm in the chitosan coating layer resulted in an approximate 30% increase in flux. Over a measurement time of 24 h, all three membranes showed a slow decrease in flux (i.e. 25% through the entire measurement time), which could be attributed to fouling, i.e. irreversible accumulation of oily particles and emulsions on the membrane surface. However, it is believed that the initial decrease in flux (<1 hr) was not due to fouling, but due to the compression of the nanofibrous supports under pressure, which decreased the effective bulk porosity and retarded the water transportation.

Under the testing conditions (130 psi, 30-33° C.), the filtration efficiency of the three membranes was also measured by monitoring the surfactant concentration of the feed solution and that of the permeate. The results are shown in Table 1. Both chitosan/PAN/PET three-tier composite membranes showed similar filtration efficiency with a rejection ratio of greater than 99.9%. This value was even slightly better than that of NF 270, which was 99.4%.

Additional modifications of the top coating layer (e.g. PEG-grafted chitosan and other hydrogels) and the reduction of coating layer thickness are expected to improve the flux rate and reduce the fouling problem.

Example 3

Top Layer Prepared by Interfacial Polymerization

Since the interfacial polymerization process requires, e.g. wetting the fibrous support with an aqueous amine solution, proper wetting and draining for the electrospun nanofibrous membrane is necessary. For this purpose, polyacrylonitrile, polysulfone, polyethersulfone, polyvinylidene fluoride, cellulose acetate, polyvinyl alcohol electrospun nanofibrous supports can be used. Depending on the hydrophilicity (or hydrophobicity) of the nanofibrous membrane, a small amount of the wetting reagent (e.g. nonionic surfactant) can also be used to enhance the wettability of relatively hydrophobic nanofibrous membranes (e.g. polysulfone, polyethersulfone, and polyvinylidene fluoride) to facilitate the interfacial polymerization process.

For reverse osmosis (RO) and nanofiltration (NF) applications, the interfacially polymerized polymer layer can comprise an aromatic amine-based solution (typically, m-phenylenediamine), with trimesoyl chloride as a crosslinking agent. Piperazine can be used as a polyfunctional monomer to fabricate membranes for NF/RO applications. For UF applications, polymeric amine(polyethyleneimine or polyvinylamine) or alcohol (polyvinyl alcohol) mixtures with a monomeric amine as an acid acceptor can be used to fabricate membranes with a higher molecular weight cutoff than RO/NF membranes.

Coating Thickness Control of Polyamide Interfacially Polymerized Containing PVA Blend on a PAN Nanofibrous Membrane by Changing Amine Concentrations Polyacrylonitrile (PAN) 8 wt % in dimethylformamide (DMF) was used to fabricate an electrospun nanofibrous support (with a typical thickness of ~40 μm, and a typical fiber diameter of ~200 nm). Different concentrations (0.05~1.0 wt %) of piperazine (PIP) were mixed with triethylamine (TEA) (1 wt %). The PAN nanofibrous support was soaked in the above solution for a few minutes. The excess amount of solution was drained out by positioning the support vertically for 2 minutes. All the edges of the resulting wet support were sealed with tape. Subsequently, trimesoyl chloride (TMC) in hexane solution (0.1 wt %) was poured onto the amine-wetted PAN nanofibrous support for 20 seconds of reaction. The excess hexane solution was drained out of the support, which was then air dried at room temperature. The membranes were extensively washed with methanol and water afterwards before they were subjected to a filtration test.

Figure 10:
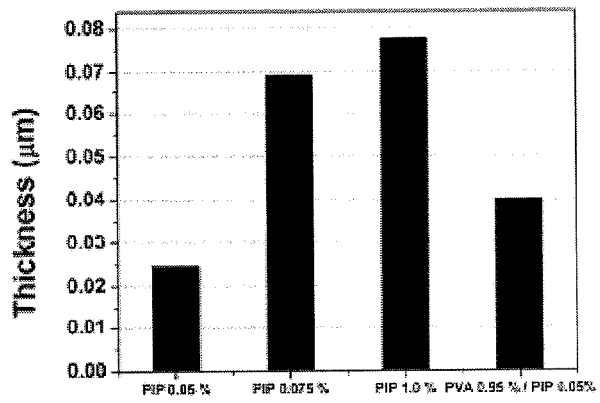
FIG. 10 shows the coating thickness of polyamide interfacially polymerized coating containing a PVA blend on a PAN nanofibrous support with changing amine concentrations.

The average coating thickness of the cross-sectional view of fractured membranes measured from more than 5 different samples by scanning electron microscopy (SEM) is shown in FIG. 10. As the concentrations of PIP were changed from 0.05% to 1.0 wt %, the coating thickness was increased from 25 nm to 75 nm (about 3 times). When PVA (MW 177 k, 88 mol % hydrolyzed) was mixed with the lowest concentration of PIP (0.05 wt %), the thickness was increased to 40 nm (vs. 25 nm for 0.05 wt % PIP only).

Pure Water flux as a Function of Reaction Time in Interfacial Polymerization

Figure 11:
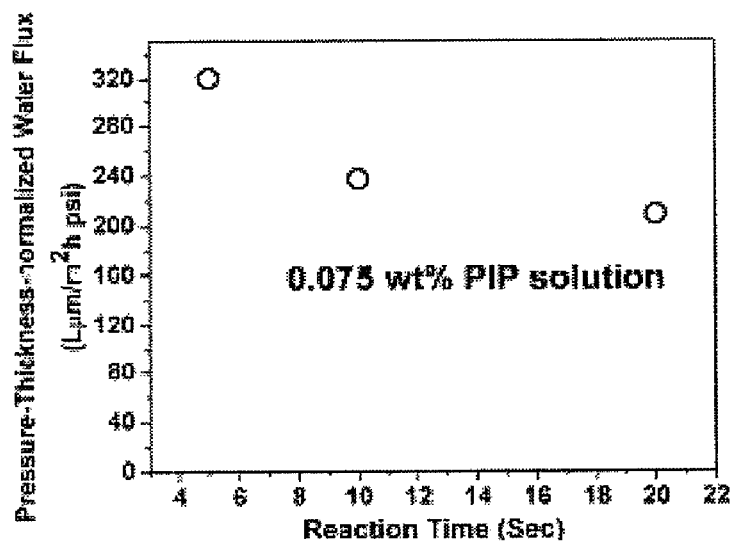
FIG. 11 shows the pure water flux (normalized by pressure and thickness) of nanofibrous membranes prepared by interfacial polymerization using different reaction times.

The pure water flux of nanofibrous membranes prepared by interfacial polymerization using different reaction time periods were measured with a dead-end cell (filtration area: 3.5 cm$^2$, at transmembrane pressure of 12 psi); the results are shown in FIG. 11. For the stable water flux measurement, all of the membranes were under compaction at 12 psi for at least 2 hours. With 0.075 wt % PIP solution, the permeate fluxes changed from 320 L·μm/m$^2$ h·psi to 210 L·μm/m$^2$ h·psi (34% decrease) with a reaction time ranging from 5 sec to 20 sec.

Figure 12:
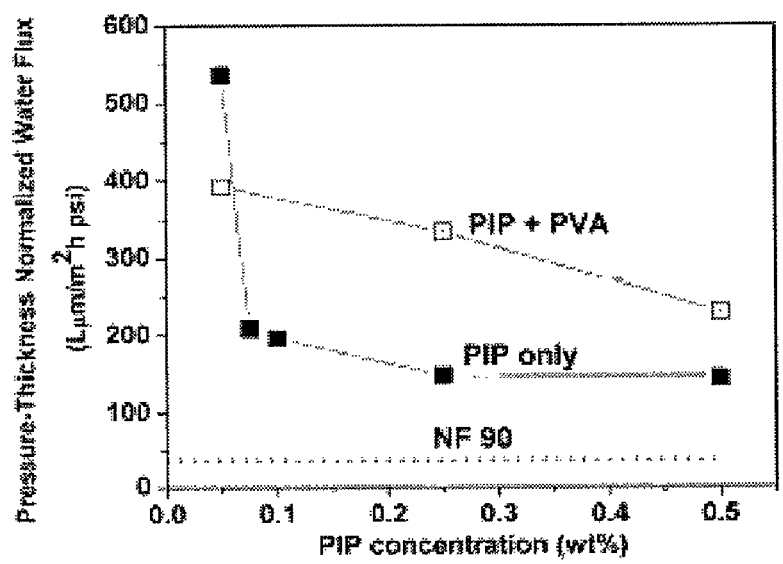
FIG. 12 shows a comparison of pure water flux (normalized by pressure and thickness) for interfacially polymerized polyamide/PVA coated PAN electrospun membranes.

Comparison of the Pure Water Flux among Nanofibrous Membranes with Interfacially Polymerized Polyamide/PVA Coating on Electrospun PAN Support with Conventional NF Membrane All of the composite membranes were prepared by the method described above, and the dead-end test condition described above. Pure water flux values are shown in FIG. 12. Even though the lowest concentration of PIP (0.05 wt %) gave the highest water flux (~550 L·μm/m$^2$ h·psi), as the PIP concentration increased up to 0.5 wt %, the flux was stabilized to around 150 L·μm/m$^2$ h·psi. The PVA mixture having PIP at the lowest concentration (0.05 wt % of PIP) exhibited a water flux lower than membranes in which the interfacially polymerized polymer layer had no PVA (PIP only). However, in the overall concentration range (up to 0.5 wt %), the mixture showed much higher (around 9 times higher flux than NF90) and relatively stable flux behavior (from 400 L·μm/m$^2$ h·psi to 250 L·μm/m$^2$ h·psi) when compared with the permeation of conventional NF 90 membrane (less than 40 L·μm/m$^2$ h·psi).

Effect of TMC Concentration on Permeate Flux and Comparison with NF270 (i.e., Piperazine-Based Nanofiltration Membrane)

A nanofibrous support (typically, 40~100 μm thickness) was soaked in an amine solution (e.g. piperazine/PEG based diamine oligomer/triethylamine, total 2 wt % in water). The amine-soaked support was drained and dried for a few minutes, then sealed along the edges with tape. A trimesoyl chloride (TMC)/hexane solution was poured on top of the membrane. Reaction times were varied from 5 sec to 30 sec, and the excess amount of hexane solution was drained out. The resulting membrane was dried for 2 hours and washed in distilled water before use.

Figure 13:
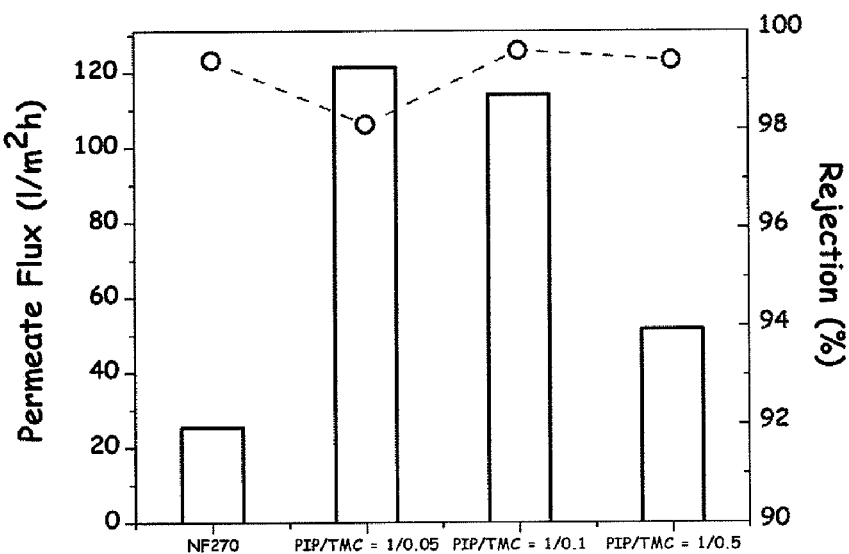
FIG. 13 shows the effect of TMC concentration on the permeate flux and rejection ratio using oil/water microemulsions and a comparison with the performance of a commercial NF270 nanofilter (i.e., a piperazine-based nanofiltration membrane).

An emulsified oil/water mixture (1350 ppm soybean oil/150 ppm DC 193 (emulsifier) in de-ionized (DI) water) was used to test ultra/nano filtration performance of these interfacially polymerized polyamide coating on polyacrylonitrile (PAN) nanofibrous membranes. A custom-built cross-flow filtration set-up was used. The active filtration area was 0.00652 m$^2$. The typical thickness of the PAN electro-spun support was 40~50 μm. The interfacially polymerized polymer coating layer thickness was about 0.3 μm, regardless of the composition of monomers used. Interfacially polymerized polymers prepared using a PIP/TMC ratio of 1/0.05 (by weight) showed the highest flux compared to other compositions, which was about 6 times higher than the NF 270 membrane flux (FIG. 13). Taking the rejection ratio (%) into account, PIP/TMC=1/0.1 had a comparable rejection value as that of NF270 with the maximum permeate flux (still 5 times higher than that of NF 270).

Figure 14:
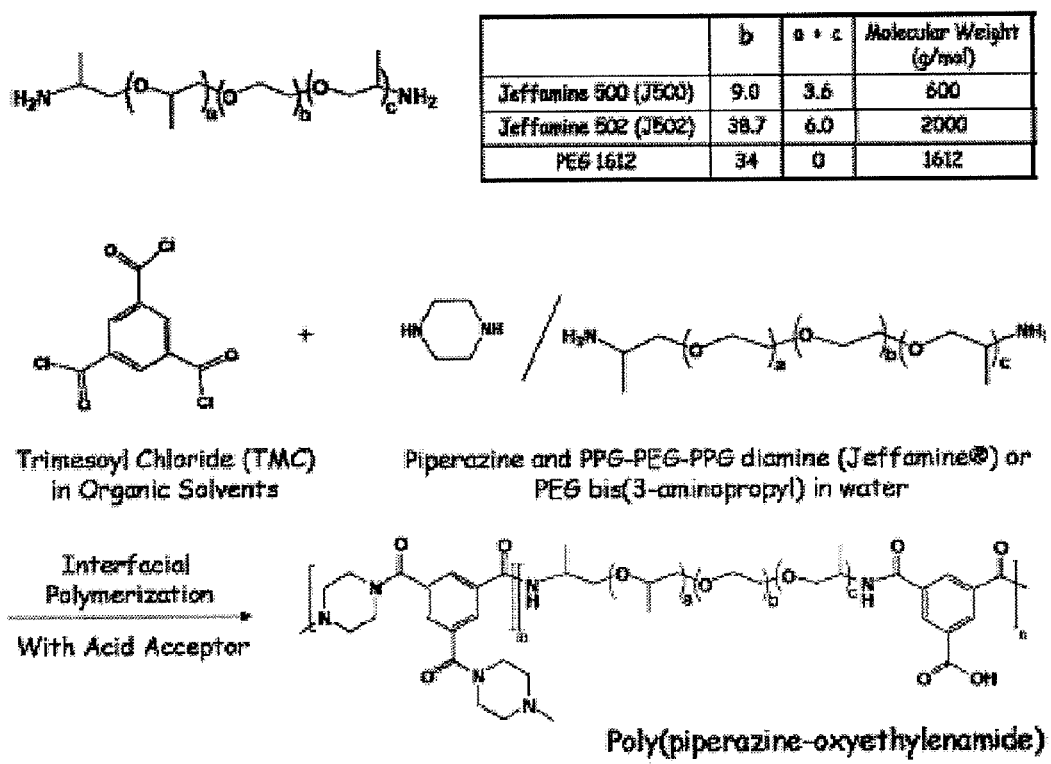
FIG. 14 shows the molecular structure of PEG-based diamines and reaction schemes for modified network structures in the top coating by interfacial polymerization.

Composition Dependence of Permeate Flux and Rejection Ratio for Hydrophilic Flexible Spacer/PIP Different structures of hydrophilic, flexible network modifiers were evaluated to increase the flux while maintaining comparable rejection (%). The molecular structures of PEG-based diamines and reaction schemes for modified network structures are shown in FIG. 14.

Figure 15:
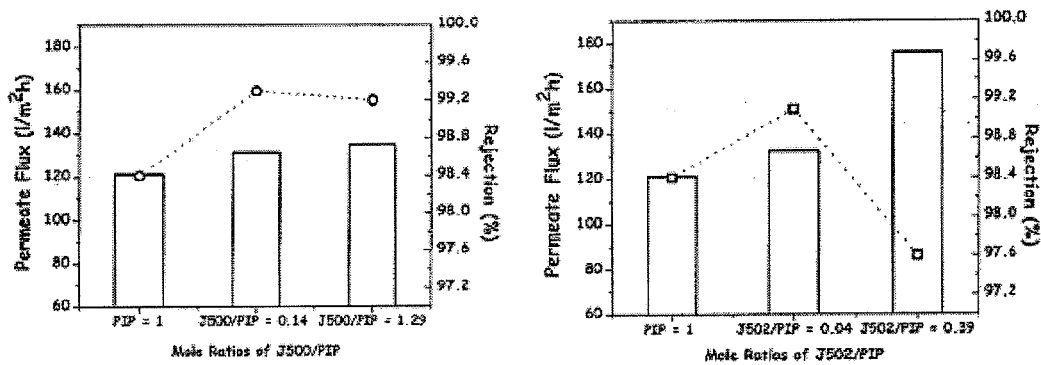
FIG. 15 shows the composition dependence of permeate flux and rejection ratio using oil/water microemulsions of polyamide top coating prepared with different Jeffamine/PIP ratios.

In FIG. 15, two different molecular weights of Jeffamine® (PEG dominant PPG-PEG-PPG copolymer) were incorporated together with PIP for the interfacial polymerization. Lower molecular weight Jeffamine (J500, PEG molecular weight ~400 g/mol) showed an 11% flux increase with improved rejection (%) (from 98.4% to 99.2%). J502 (PEG molecular weight ~1700 g/mol), showed a 45% flux increase with respect to that of PIP only layer, but rejection (%) had slightly decreased from 98.4% to 97.6%. Low molecular weight Jeffamine seemed to have better flux and rejection (%) than high molecular weight Jeffamine.

Figure 16:
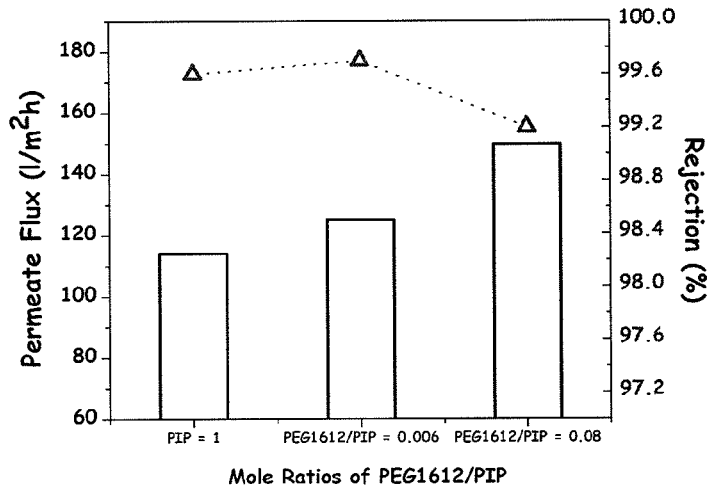
FIG. 16 shows the composition dependence of permeate flux and rejection ratio using oil/water microemulsions of polyamide top coating prepared with different PEG1612/PIP ratios.

In FIG. 16, PEG bis(3-aminopropyl) diamine was used to modify the basic PIP/TMC interfacial polymerization composition. A PEGI 612/PIP molar ratio of 0.08 showed the best performance (flux: 31% increase, rejection ratio (%): 99.2%). Compared to Jeffamines, PEG1612 had a slightly higher permeate flux (~150 l/m$^2$ h) than J500 (~135 l/m$^2$ h).

Hydraulic Resistance Test for Different Compositions of PEG1612/PIP Coating

Figure 17:
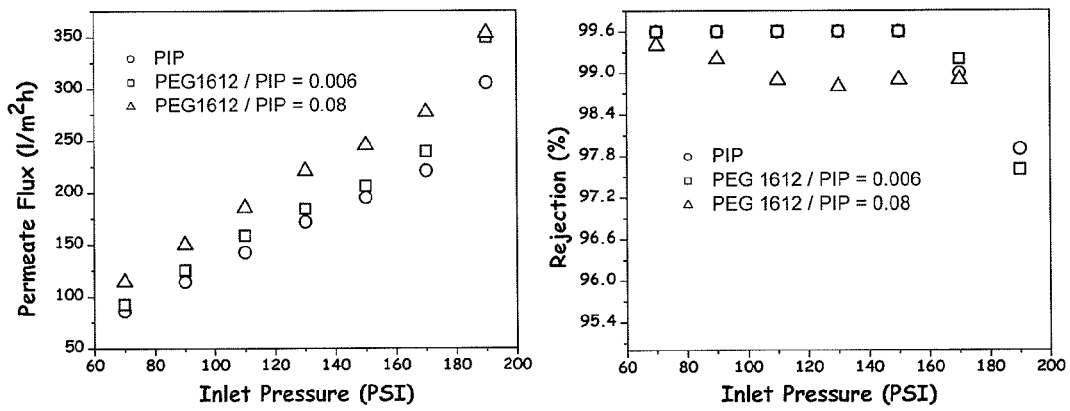
FIG. 17 shows the hydraulic resistance test results for nanofibrous membranes containing different compositions of PEG 1612/PIP coating.

The membranes with PEGI 612/PIP coatings described above were tested for applied pressure-dependent hydraulic resistance (FIG. 17). Regardless of the compositions, all coatings were stable up to 170 psi without substantial rejection loss (~99%). Hydraulic permeability was found to be linear with respect to applied pressure for all compositions.

Figure 18:
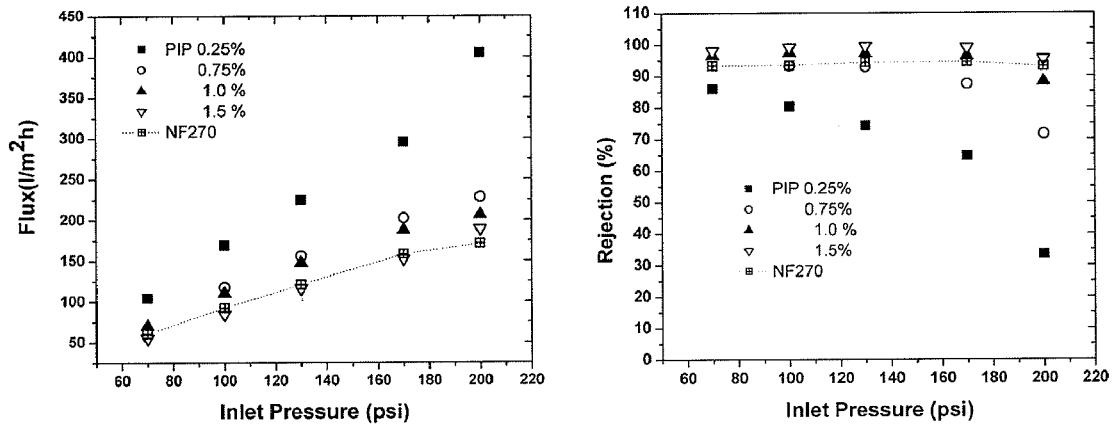
FIG. 18 shows the pressure dependence on permeate flux and rejection for interfacially polymerized PIP/TMC coated electro-spun PAN membrane and NF 270.

Nanofiltration Performance Comparison Between Conventional UF Membrane and Electrospun Membrane as a Mid Layer for Interfacially Formed Polyamide Coating In FIG. 18, various piperazine (PIP) concentrations in aqueous solution were interfacially reacted with 0.1 w/v (%) TMC/hexane to fabricate an ultrathin polyamide coating on PAN electrospun supports. The magnesium sulfate (2000 ppm) filtration performance at different inlet pressures was evaluated. The permeate flux was 30% higher than conventional NF 270 membrane throughout 100~200 psi range. The rejection % is similar to NF 270 performance (95% rejection) for all of the operating pressure range.

Nanofiltration Performance of Mixed Amine(Bipiperidine/Piperazine) System for Interfacially Polymerized Polyamide Coating on PANE-Spun Membrane vs. NF 270

Figure 19:
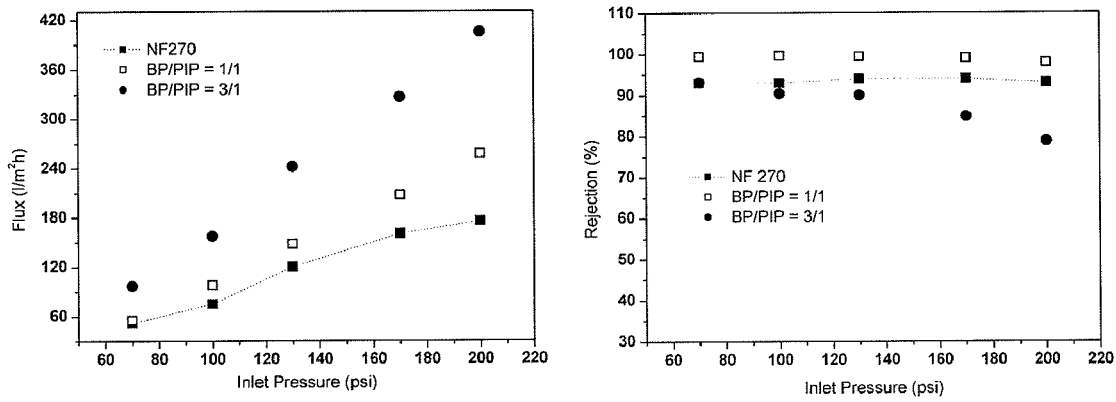
FIG. 19 shows the pressure dependence on permeate flux and rejection for interfacially polymerized BP/PIP/TMC coated electro-spun PAN membrane and NF 270.

4,4'-Bipiperidyl dihydrochloride (BP) was mixed with PIP (total concentration: 0.25 wt %), and the pH was adjusted to 10~13 using 5 M NaOH, depending on the amount of BP. After adding sodium dodecyl sulfate (0.375 w/v (%) with respect to the total volume), the mixed amine solution was reacted at the surface of electrospun PAN supports with 0.1 w/v (%) TMC/hexane solution for 20 sec. The permeate flux and rejection (%) was tested using 2000 ppm of magnesium sulfate. In FIG. 19, when the amine ratio BP/PIP is about 1/1, the rejection ratios are higher (>98%) than NF 270 (93~94%) for the operation range (70~200 psi). In addition, the permeate flux was 47% higher at 200 psi than NF 270. When the BP/PIP ratio is 3/1 at 70 psi, the permeate flux increased 86% with the similar rejection (~93%) compared to NF 270.

Reverse Osmosis Performance Comparison between Conventional UF Membrane and Electrospun Membrane as a Mid Layer for Interfacially Formed Polyamide Coating Trimesoyl chloride (TMC) 0.1 w/v % in hexane was reacted with 1 w/v % m-phenylenediamine (MPD) to form a semi-permeable coating layer on nanofibrous substrate, and the resulting membranes were evaluated using a 2000 ppm NaCl feed solution. The reaction time was 20 sec. and the membrane was washed with 0.2 w/v % sodium carbonate solution and thoroughly washed with water. The same coating conditions were used to compare two different substrates (conventional UF membrane (PAN400, MWCO: 20 k PVA 75%) and a PAN electro-spun support). At an inlet pressure of 150 psi, the UF membrane based thin film composite showed 3.87 L/m$^2$ h with 85.7% rejection. At the same inlet pressure, the PAN electro-spun membrane based thin film composite showed 7.73 L/m$^2$ h with 98.6% rejection rate. Thus, the PAN electro-spun membrane combined with a TMC/MPD interfacial coating has a 2 times higher permeation flux than conventional UF membrane based thin film composite, and a higher rejection rate.

Figure 20:
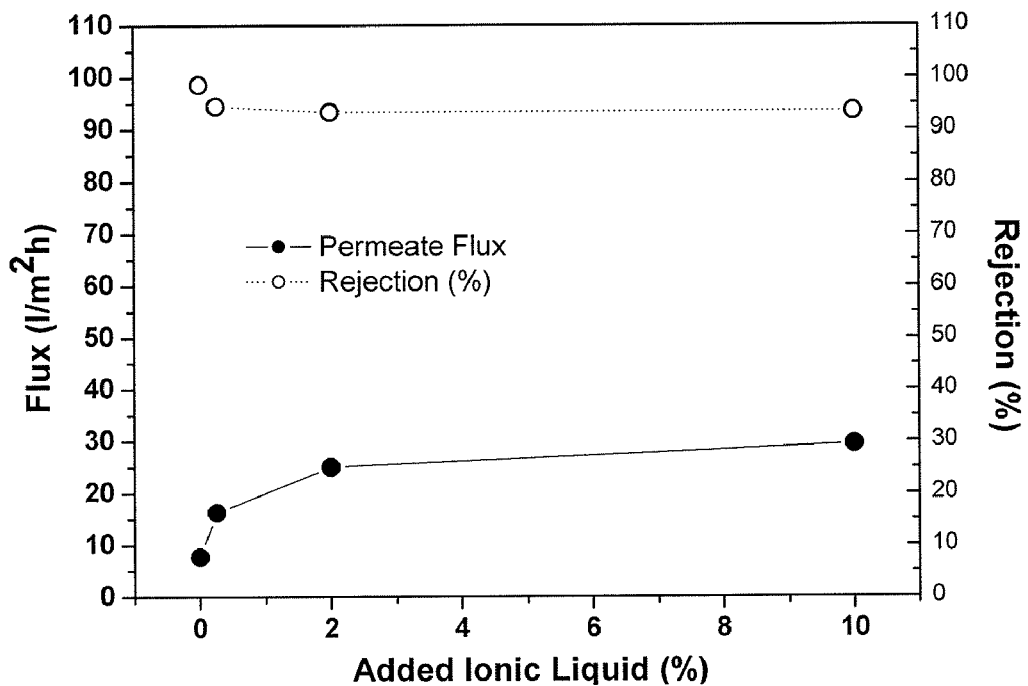
FIG. 20 shows the effects of incorporating ionic liquid (1-butyl-3-methylimidazolium chloride) in the amine solution on interfacially polymerized polyamide coating of electro-spun PAN membrane.

Effect of Room Temperature Ionic Liquids (RTILS) as an Additive for Aqueous Amine Phase in Interfacial Polymerization on Electrospun Membrane 1-butyl-3-methylimidazolium chloride was added to 1 w/v (%) m-phenylenediamine solution (0.26~10 w/v (%)). A 0.1 w/v (%) TMC/hexane solution was reacted for 20 seconds at the surface of the ionic liquid/amine solution-soaked electrospun PAN membrane. The flux and rejection (%) of the membranes was evaluated in a cross-flow cell at 150 psi with 2000 ppm of NaCl solution. In FIG. 20, with the increase of the ionic liquid in the amine solution up to 10 w/v (%), the maximum permeate flux was 3.8 times higher than for compositions containing no ionic liquid, and the rejection was only reduced slightly, from 98% (for 0% ionic liquid) to 94% (for 10% ionic liquid).

Figure 21:
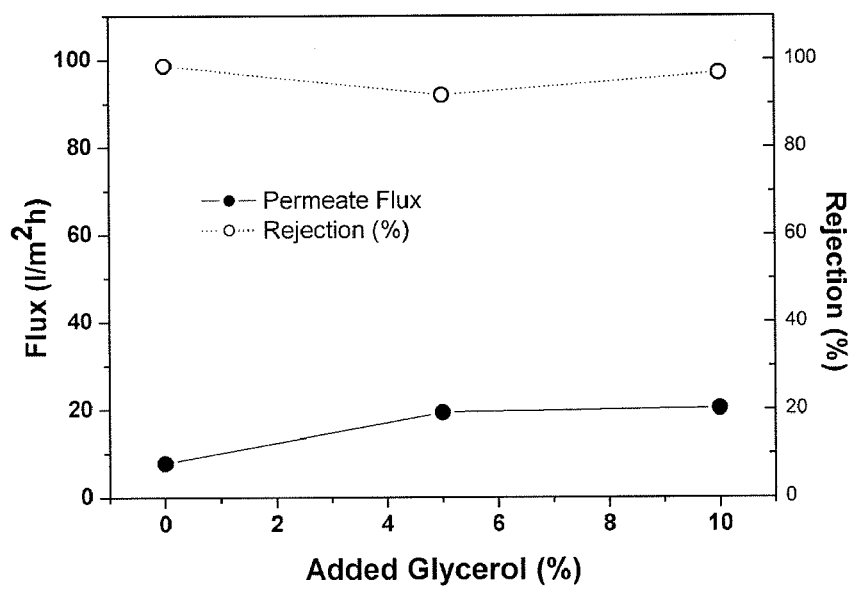
FIG. 21 shows the effects of incorporating glycerol on the amine solution on interfacially polymerized polyamide coating of PAN electro-spun membrane.

Effect of Glycerol as an Additive on Interfacially Formed Polyamide Coating Layer The effect of glycerol on an interfacially polymerized polyamide coating was tested using glycerol (up to 10 w/v (%)) in an aqueous m-phenylenediamine solution. The permeate flux and rejection (%) was tested by using 2000 ppm of NaCl solution with a cross-flow cell. FIG. 21 shows that as the amount of glycerol increased, the permeate flux was increased by a factor of 2.6 (compared to pure m-phenylenediamine case). The rejection decreased slightly from 98% to 97% (for 10% glycerol)

Effect of Sulfonated/Carboxylated Phenylene Diamine as Comonomers on Interfacially Formed Polyamide Coating Layer 3,5-diamino benzenesulfonic acid and/or 3,5-diaminobenzoic acid can be incorporated into interfacially polymerized polyamide coating layer when mixed with m-phenylene diamine (MPD). The sulfonic acid/carboxylic acid group can be easily ionized under neutral pH condition, and become charged. Since the molecular structures of diamines (sulfonated and carboxylated) are similar to m-phenylene diamine, the reactivity difference between MPD and these amines is not as large as when they are mixed with an aliphatic cyclic diamine (e.g. piperazine), which sometimes leads to adverse results (lower flux and lower rejection). The amount of the above acid-functional amines in MPD should be less than 10% in order not reduce the rejection too much.

Example 3

Top Layer Prepared by PVA Solution Casting

Figure 22:
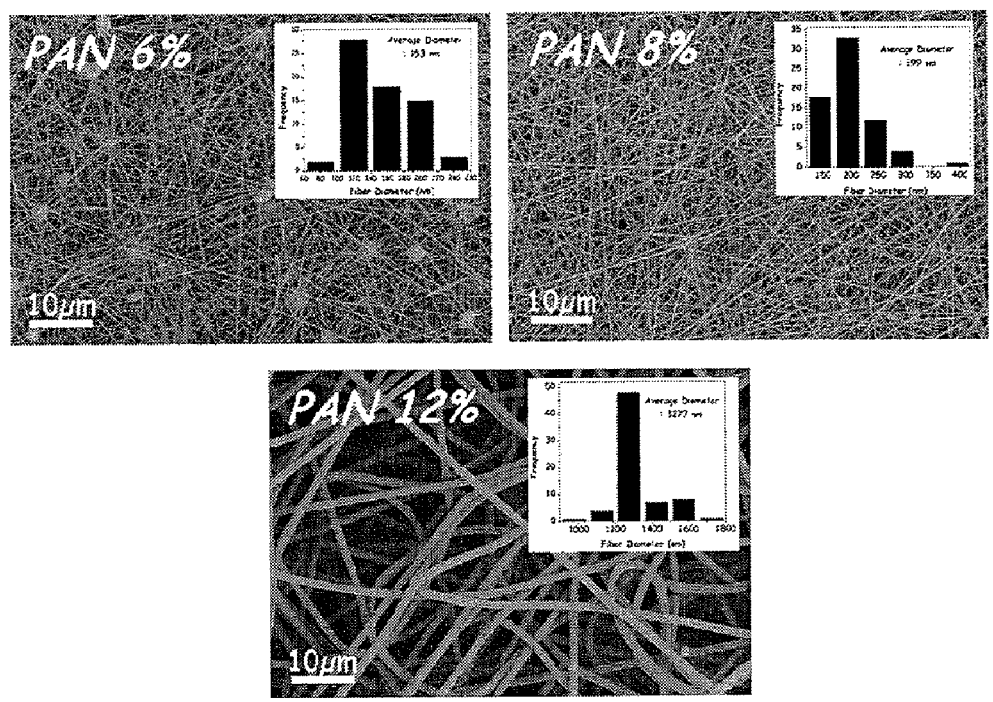
FIG. 22 shows the concentration dependence of PAN electro-spun fiber diameters.
Figure 23:
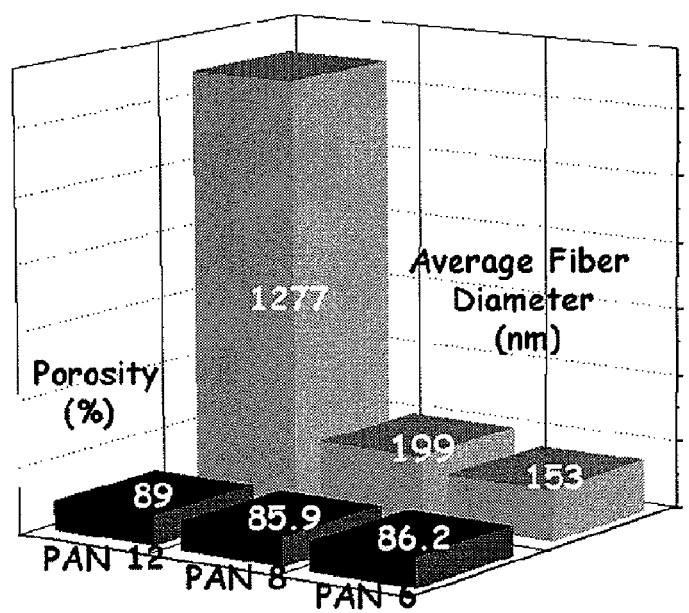
FIG. 23 provides comparisons of each electro-spun PAN fiber diameters and their membrane porosities.
Figure 24:
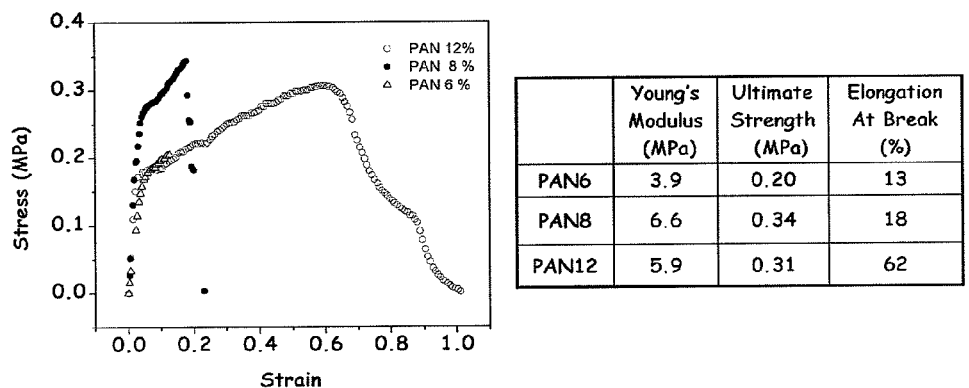
FIG. 24 shows stress-strain curves of PAN electro-spun membranes.

PAN electrospun fiber diameters can be controlled by varying different parameters, such as solution concentration, electric field strength, pump speed, and so on. In this example, only the concentration was changed (from 6 wt % to 12 wt %) in order to vary the fiber sizes. Fiber sizes were changed from 153 nm to 1277 nm, depending on solution concentrations (FIG. 22). The support porosity remained relatively constant (with changes of less than ~3%) while the fiber size changed by ~88% (FIG. 23). It was found to be desirable to minimize the fiber roughness and maintain good mechanical properties in the electrospun mid-layer in order to support a thin and flawless top-coating layer on the membrane surface. From the stress-strain curves (FIG. 24) of PAN electrospun membranes, PAN 8% showed the highest modulus and strength values, which are most appropriate for our study and were used.

Figure 25:
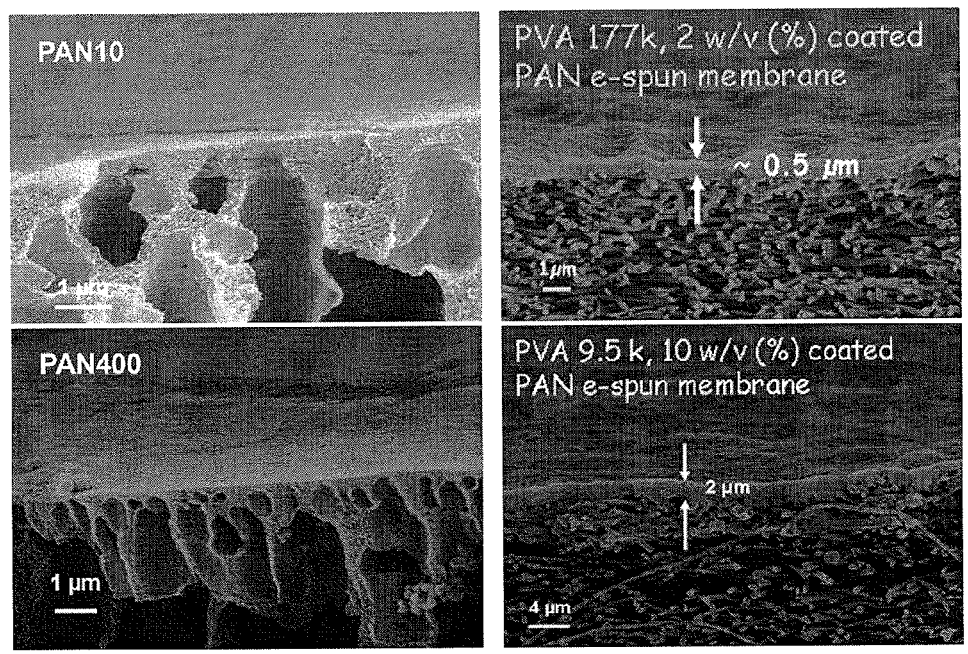
FIG. 25 shows SEM images of commercial UF membranes and PVA-PAN e-spun membranes.

Based on the PAN 8 electrospun membrane, a PVA coating was successfully applied without serious defects (e.g. holes). Typical SEM cross-sectioned views of PVA(177 k and 9.5 k)-coated PAN 8 composite membranes and conventional PAN UF membranes are shown in FIG. 25, revealing the clear structural difference between the two systems. The commercial PAN UF membrane has an asymmetric pore structure and no additional selective coating layer.

Figure 26:
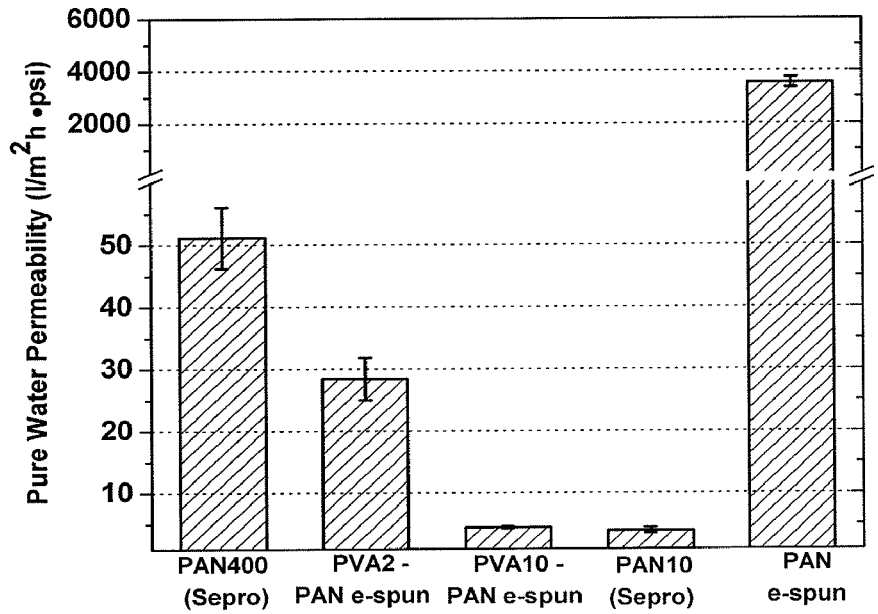
FIG. 26 shows the pure water permeabilities of commercial UF membranes vs. PVA-PAN electro-spun membranes (Note: PVA2=PVA 177 k, PVA10=PVA 9.5 k).

Pure water permeabilities for all membranes were measured using a dead-end cell (filtration area: 11.5 cm$^2$, Advantec UHP43) with the pressurized nitrogen gas. Deionized (from Milli Q) water was used for all samples. Commercial PAN UF membrane thicknesses are about 150 µm and PVA-coated (and PAN electro-spun support only) PAN electro-spun supports are about 140 µm (including PET non-woven thickness (~100 µm)). The pressure-normalized water fluxes (i.e. water permeabilities) (FIG. 26) indicated that PAN electro-spun support itself showed very high flux versus all the other membranes (~3000 l/m$^2$ h), which is due to the fact that it has fully interconnected pore structure and large surface pores. PVA-coated PAN electro-spun membranes showed the intermediate permeability between PAN400 and PAN10 commercial ultrafiltration (UF) membranes.

In order to compare the sieving property of the membranes, several molecular weights of dextrans were used (64~76 k, 35~45 k, and 9~11 k) to evaluate the molecular weight cut-offs (typically defined as 90% rejection of PEG or Dextran marker molecules). With the dead-end cell (Advantec, UHP43), 0.5 wt (%) of the feed solution for each dextran grade with 0.05 wt (%) sodium azide was used for the evaluation (Table 1). The feed and permeate concentrations were checked using a total organic carbon analyzer with the calibrated standard concentrations of each dextran grade. Even though PAN 400 (Sepro) showed the highest water permeability (50 L/m$^2$ h·psi), the rejection (%) for all molecular weight ranges are much lower (less than 10%) than other membranes, probably due to the large effective pore size distribution. PVA-PAN electro-spun membrane showed the higher rejection (%) compared to commercial PAN UF membranes, kept higher water permeability (29 l/m$^2$ h·psi) than PAN10's (4 l/m$^2$ h·psi).

Figure 27:
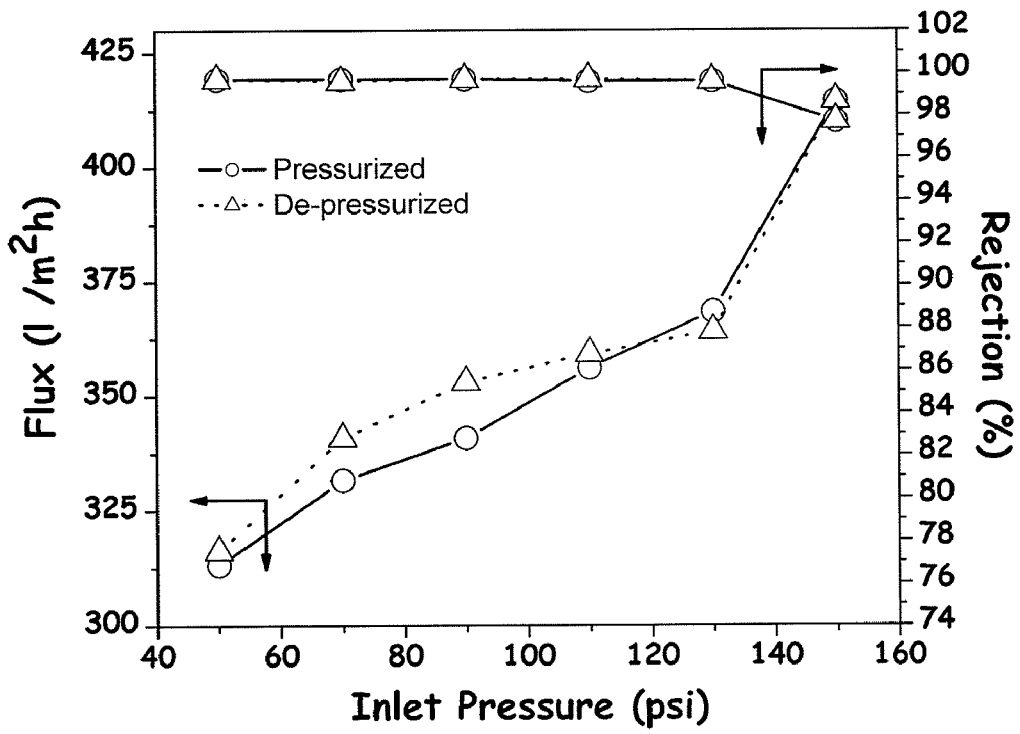
FIG. 27 shows the pressure dependence of oily water filtration.

The pressure-dependent permeate flux and rejection rate were measured using PVA 177 k as a coating layer for oily waste feed solution. The results are shown in FIG. 27. The applied inlet pressures were ranged from 50 to 130 psi, which are typically used in UF applications. The PVA177 k coated PAN e-spun membrane showed the good hydraulic pressure resistance (up to 130 psi) with good rejection efficiency. The permeate flux showed reversible behavior upon the pressurizing-depressurizing protocol, which is indicating "elastic" nature of hydrogel coating layers.

Figure 28:
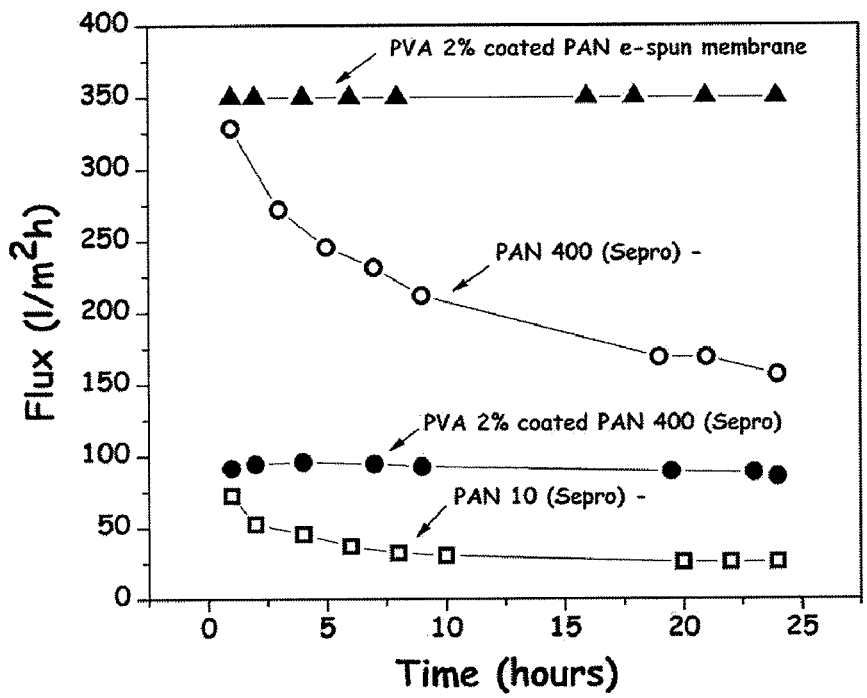
FIG. 28 shows emulsified oily water filtration for 24 hours.

During 24 hours of continuous filtration with emulsified oily water (1350 ppm of soybean oil and 150 ppm of DC193 Fluid) in FIG. 28, PVA-coated PAN electro-spun membrane showed very stable permeate flux compared to commercial PAN UF membranes. Both PAN UF membranes permeate fluxes were reduced to more than 50% of initial fluxes, probably due to severe membrane surface fouling by oily emulsion. The stable flux of PVA coated PAN e-spun membranes could be due to the antifouling property of PVA. In order to investigate the antifouling property of PVA coating layer, the same PVA coating composition was applied to PAN400 UF membrane for the coating. PVA-coated PAN400 showed the stable permeate flux during the filtration, but bigger hydraulic resistance of PAN UF membrane support layer than that of PAN e-spun membrane reduces the overall permeate flux. The productivity (i.e. permeate flux) is reduced to about a factor of 3 for PVA-coated PAN 400 UF membrane's when it compares to PVA-coated PAN e-spun membranes.

Figure 29:
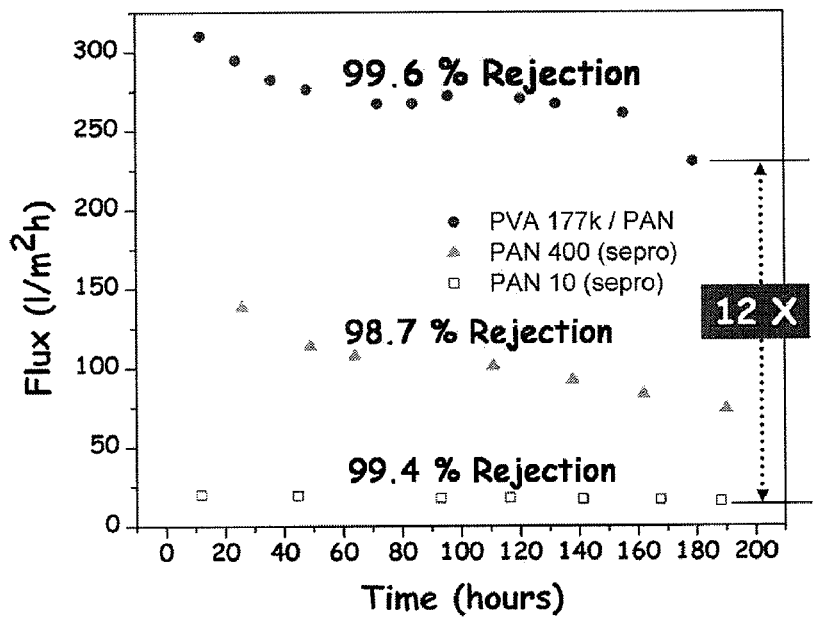
FIG. 29 shows emulsified oily water filtration for 190 hours.

A PVA 235 coated PAN 8 electro-spun membrane was tested for long-term filtration (~190 hours) using oily waste water at 90 psi (FIG. 29). Compared to two commercial PAN UF membranes, the PVA/PAN composite membrane showed 3 times (for PAN 400) and 12 times (for PAN 10) higher fluxes than commercial membranes, respectively. Notably, both commercial membranes have lower rejection rate (%) than PVA/PAN membranes. The flux decline (26%) for PVA/PAN composite membrane was slightly higher (20% for PAN 10) or better (47% for PAN 400) than commercial PAN UF membranes.

Figure 30:
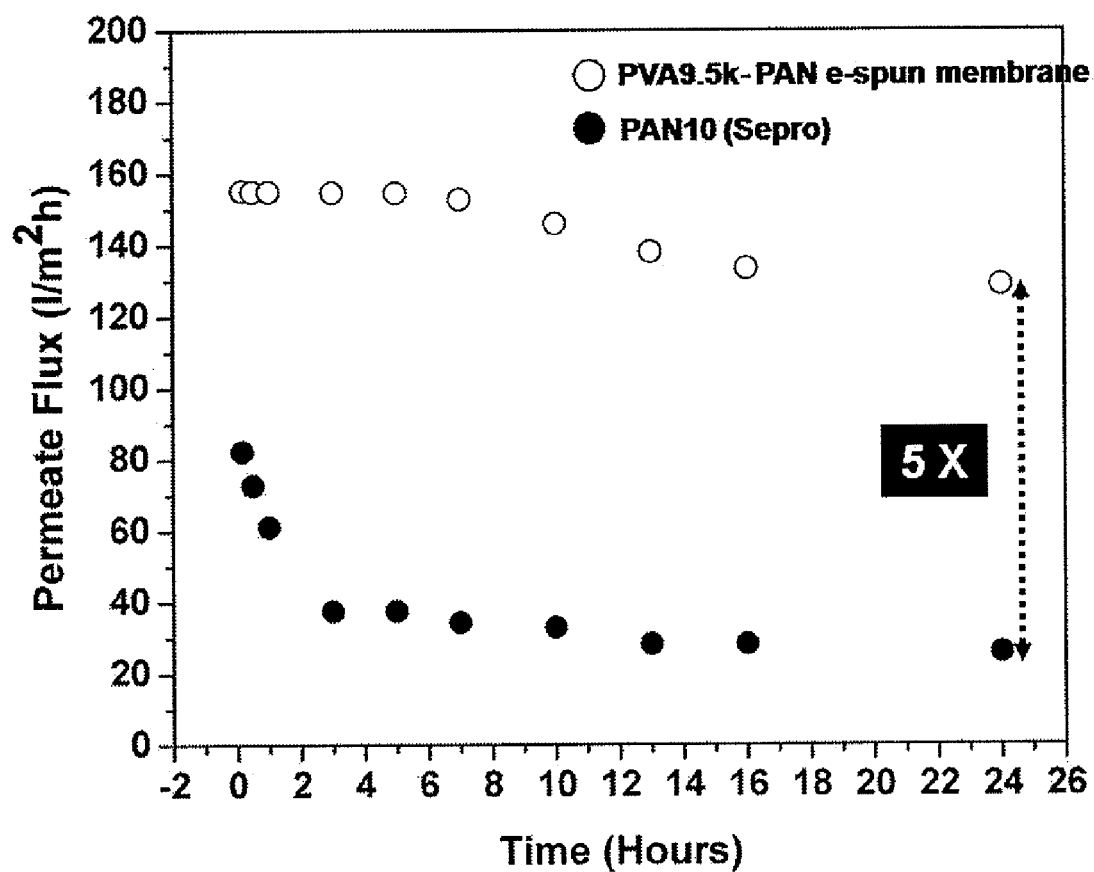
FIG. 30 shows sodium alginate (80~120 kDa, 500 ppm) filtration for 24 hours.

To prove versatile antifouling properties for PVA coating-based membranes to different foulants, sodium alginate (80~120 kDa, 500 ppm) was used for the filtration test. In FIG. 30, PVA 9.5 k coated PAN e-spun membrane showed only 16% decreased permeate flux compared to the initial flux after 24 hours of continuous filtration, but for PAN 10, the permeate flux decreased 80% of the initial flux. All the filtration period, sodium alginate rejection was maintained to higher than 99% for both cases. Eventually 5 times higher permeate flux has been observed for PVA coated PAN e-spun membrane than PAN UF membranes.

While various embodiments of the present invention have been illustrated and described in detail, various modifications of, for example, components, materials and parameters, will become apparent to those skilled in the art, and all such modifications and changes are intended to fall within the scope of the claims of the present invention.

All patents, patent applications, and other documents referenced herein are incorporated by reference in their entirety for all purposes, unless otherwise indicated.

We claim:
1. An article comprising:
    a fibrous support comprising nanofibers, the fibrous support having a thickness from 5 µm to about 50 µm; and
    an interfacially polymerized polymer layer disposed on a surface of the fibrous support,
    wherein the interfacially polymerized polymer layer further comprises at least one hydrophilic or hydrophobic nanoparticulate filler.
2. The article of claim 1, wherein the nanofibers have an average diameter ranging from about 2 nm to about 2000 nm.
3. The article of claim 1, wherein:
    the fibrous support is in the form of a sheet comprising a top layer and a bottom layer;
    the top layer is disposed between the interfacially polymerized polymer layer and the bottom layer;
    each of the top and bottom layers is comprised of nanofibers; and
    the average diameter of the nanofibers of the top layer is less than the average diameter of the nanofibers of the bottom layer.
4. The article of claim 3, wherein the average diameter of the nanofibers of the top layer ranges from about 2 nm to about 500 nm, and the average diameter of the nanofibers of the bottom layer ranges from about 500 nm to about 50 µM.
5. The article of claim 3, wherein the thickness of the interfacially polymerized polymer layer ranges from about 10 nm to about 500 nm.
6. The article of claim 3, wherein:
    the fibrous support further comprises a middle layer comprised of nanofibers disposed between the top layer and bottom layer; and
    the average diameter of the nanofibers of the middle layer is:
    less than the average diameter of the nanofibers of the bottom layer, and greater than the average diameter of the nanofibers of the top layer.
7. The article of claim 6, wherein the average diameter of the nanofibers of the top layer ranges from about 2 nm to about 500 nm, the average diameter of the nanofibers of the middle layer range from about 10 nm to about 500 nm, and the average diameter of the nanofibers of the bottom layer are 500 nm or more.
8. The article of claim 6, wherein the thickness of the interfacially polymerized polymer layer ranges from about 2 nm to about 500 nm.
9. The article of claim 3, further comprising a substrate layer disposed on the bottom layer, whereby the bottom layer is disposed between the substrate layer and the top layer.
10. The article of claim 9, wherein the substrate layer is a nonwoven fabric.
11. The article of claim 10, wherein the fibers of the nonwoven fabric comprise at least one material selected from the group consisting of poly(ethylene terephthalate), polypropylene, cellulose, polyamide, polyurethane, glass, inorganic fibers, and metallic fibers, their derivatives, and combinations thereof.
12. The article of claim 9, wherein the substrate layer has an average thickness of from about 20 µm to about 20 mm.

13. The article of claim 6, further comprising a woven or nonwoven substrate layer disposed on the bottom layer, whereby the bottom layer is disposed between the substrate layer and the middle layer.

14. The article of claim 1, wherein the nanofibers at the surface of the fibrous support penetrate the interfacially polymerized polymer layer from about 1% to about 100% of the thickness of the interfacially polymerized polymer layer.

15. The article of claim 1, wherein the nanoparticulate filler comprises at least one hydrophilic nanoparticulate filler selected from the group consisting of oxidized carbonaceous nanoparticles, surface grafted carbonaceous nanoparticles, water dispersible nanoclays, and combinations thereof.

16. The article of claim 15, wherein the nanoparticulate filler comprises an oxidized carbonaceous nanoparticle selected from the group consisting of oxidized single-walled carbon nanotubes, oxidized multi-walled carbon nanotubes, oxidized carbon nanofibers, and oxidized graphene sheets.

17. The article of claim 15, wherein the nanoparticulate filler comprises a carbonaceous nanoparticle surface grafted with oligomeric or polymeric water-soluble polymers; and
the carbonaceous nanoparticles surface grafted with oligomeric or polymeric water-soluble polymers are selected from the group consisting of single-walled carbon nanotubes, multi-walled carbon nanotubes, carbon nanofibers, and graphene sheets.

18. The article of claim 15 wherein the nanoparticulate filler comprises a water dispersible nanoclay selected from the group consisting of lucentite and montmorillonite clays.

19. The article of claim 16, wherein the nanofiber filler has an average diameter of from about 2 nm to about 2000 nm.

20. The article of claim 1, wherein the interfacially polymerized polymer layer further comprises a functionalized molecule.

21. The article of claim 20, wherein the functionalized molecule is selected from the group consisting of a hydrophobic molecules, hydrophilic molecules, organic molecules, inorganic molecules, organic-inorganic polymer composites, antibodies, antigens, DNA, RNA, proteins, peptides, positively charged molecules, negatively charged molecules, amphiphilic molecules, and combinations thereof.

22. The article of claim 1, wherein the interfacially polymerized polymer layer comprises a polymer selected from the group consisting of a crosslinked or uncrosslinked polyamide, a crosslinked or uncrosslinked polyimide, a crosslinked or uncrosslinked polyester, a crosslinked or uncrosslinked polyurea, a crosslinked or uncrosslinked polyurethane, a crosslinked or uncrosslinked polysulfone, a crosslinked or uncrosslinked polycarbonate, derivatives thereof, and combinations thereof.

23. The article of claim 1, wherein the nanofibers comprise a polymer selected from the group consisting of polyolefins, polysulfones, polyethersulfones, fluoropolymers, polyvinylidene fluorides, polyesters, polyamides, polycarbonates, polystyrenes, polyacrylamides, polyacrylates, polyacrylonitriles, poly(meth)acrylates, polyvinyl acetates, polyvinyl alcohols, polysaccharides, chitosan, proteins, polyalkyleneoxides, polyurethanes, polyureas, polyvinyl chlorides, polyimines, polyvinylpyrrolidones, polyacrylic acids, polymethacrylic acids, polysiloxanes, poly(ester-co-glycol) polymers, poly(ether-co-amide) polymers, cross-linked forms thereof, derivatives thereof and copolymers thereof.

24. The article of claim 23, wherein the nanofibers comprise polyamide, polyacrylonitrile, polysulfone, polyvinyl alcohol, or derivatives thereof.

25. The article of claim 23, wherein the nanofibers comprise a polymer functionalized with a hydrophilic group.

26. A membrane comprising the article of claim 1.

27. The membrane of claim 26, wherein the membrane is an ultrafiltration membrane, a nanofiltration membrane, a reverse osmosis membrane, or a forward osmosis membrane.

28. A membrane module comprising:
at least one membrane of claim 26;
means of contacting a fluid mixture with the surface of the interfacially polymerized polymer layer of the at least one membrane;
means for removing a retentate from the surface of the interfacially polymerized polymer layer; and
means for removing a permeate from the surface of the fibrous support opposite the surface of the fibrous support contacting the interfacially polymerized polymer layer.

29. The membrane module of claim 28, wherein the membrane module is a spiral wound membrane module or a flat sheet membrane module.

30. A fluid separation system comprising at least one membrane module of claim 28.

31. A fluid separation system comprising at least one membrane module of claim 29.

* * * * *